(12) United States Patent
Miller et al.

(10) Patent No.: US 6,756,054 B1
(45) Date of Patent: Jun. 29, 2004

(54) POLYCATIONIC STEROL DERIVATIVES AS TRANSFECTION AGENTS

(75) Inventors: Andrew D. Miller, London (GB); Robert G. Cooper, London (GB); Christopher J. Etheridge, London (GB)

(73) Assignee: IC-VEC Limited, London (GB)

( * ) Notice: Subject to any disclaimer, the term of this patent is extended or adjusted under 35 U.S.C. 154(b) by 0 days.

(21) Appl. No.: 09/194,267

(22) PCT Filed: May 23, 1997

(86) PCT No.: PCT/GB97/01426

§ 371 (c)(1),
(2), (4) Date: Mar. 22, 1999

(87) PCT Pub. No.: WO97/45442

PCT Pub. Date: Dec. 4, 1997

(30) Foreign Application Priority Data

May 24, 1996 (GB) .............................. 9610944
Mar. 17, 1997 (GB) .............................. 9705498

(51) Int. Cl.[7] .................. A61K 9/127; C12N 15/88

(52) U.S. Cl. .................................. 424/450; 435/458

(58) Field of Search ............... 514/44, 42; 424/450, 424/1.2; 435/6, 325; 252/357

(56) References Cited

U.S. PATENT DOCUMENTS 5,767,099 A * 6/1998 Harris et al.

FOREIGN PATENT DOCUMENTS

WO    WO 96/10038    * 4/1996

OTHER PUBLICATIONS

Moradpour et al. Biochemical and Biophysical Research Communications, vol. 221, pp. 82–88, Apr. 1996.*

* cited by examiner

*Primary Examiner*—Sean McGarry
*Assistant Examiner*—Janet L. Epps-Ford

(57) ABSTRACT

A compound capable of acting as a cationic lipid is described. The compound comprises a cholesterol group having linked thereto a head group; wherein the head group is more positive than the head group of DC-Chol.

22 Claims, 23 Drawing Sheets

DOTMA   N-[1-(2,3-dioleoyloxy)propyl]-N,N,N-trimethyl ammonium chloride

DOPE   Dioleoylphosphatidyl ethanolamine

Figure 1:
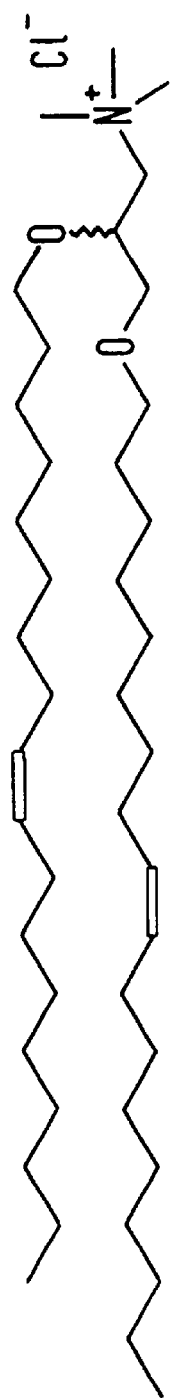

3β-[(N,N-dimethylamino ethyl)carbamoyl]cholesterol
DC-Chol

2, R = C(O)OChol
3, R = H

Scheme 1

Scheme 2 Reagents and conditions: i, $CH_2Cl_2$ (0.2M), $PhCH_2OC(O)Cl$ (0.45 eqv), 10h; ii, $CH_2Cl_2$ (0.2M), $Et_3N$ (3 eqv), $CH_3SO_2Cl$ (2.5 eqv) 0°C to r.t., 15min; iii, DMF (0.15M), $NaN_3$ (5 eqv), NaI, 80°C, 2h

|  | 6a | 6b | 6c | 7a | 7b | 7c | 4a | 4b | 4c |
|---|---|---|---|---|---|---|---|---|---|
| m | 1 | 2 | 3 | 1 | 2 | 3 | 1 | 2 | 3 |
| YIELD / % | 89 | 86 | 92 | 97 | 88 | 95 | 98 | 90 | 96 |

Table 1

Scheme 3 Reagents and conditions: i, CH$_2$Cl$_2$ (0.2M), CholOC(O)Cl (0.45 eqv), 5h; ii, a, CH$_2$Cl$_2$ (0.1M) (COCl)$_2$ (1.5 eqv), DMSO (3 eqv), -78°C, 15min; b, 8, 15 min; c, $i$-Pr$_2$NEt (3 eqv) to r.t.

| n | 8a | 8b | 9a | 9b |
|---|---|---|---|---|
|  | 1 | 2 | 1 | 2 |
| YIELD / % | 98 | 99 | 97 | 93 |

Table 2

Table 3

Scheme 4 Reagents and conditions: i, a, THF (0.5M), 4 Å molecular sieves, PMe3 (1.15 eqv), 30 min; b, 9 (1.1 eqv), 3h; c, EtOH (0.5M), NaBH$_4$ (2 eqv), 20 h; ii, EtOH (0.2M), c-C$_6$H$_{10}$ (20 eqv), 10% Pd(C) (0.5 eqv), reflux, 30 min

|   | 10a | 10b | 10c | 10d | 10e | 10f | 2a | 2b | 2c | 2d | 2e | 2f |
|---|-----|-----|-----|-----|-----|-----|----|----|----|----|----|----|
| m | 1   | 2   | 3   | 1   | 2   | 3   | 1  | 2  | 3  | 1  | 2  | 3  |
| n | 1   | 1   | 1   | 2   | 2   | 2   | 1  | 1  | 1  | 2  | 2  | 2  |
| YIELD / % | 79 | 72 | 89 | 83 | 87 | 90 | 99 | 99 | 99 | 99 | 99 | 99 | i) MeSO$_2$Cl (2.5 eq), NEt$_3$ (3 eq), DCM, 0°C, 0.3 hrs.; ii) NaBr (5 eq), NaI (1 eq), DMF, 80°C, 2 hrs; iii) K$_2$CO$_3$ (2 eq), NaI (0.3 eq), H$_2$NC(CH$_2$)$_n$OH (5 eq), DMF, 24-72 hrs; iv) PhOCOCl (1.1 eq), NEt$_3$ (2.5 eq), DCM, 6 hrs

OVERALL YIELDS 74-88% i) TBDPS-Cl (1.5 eq), NEt$_3$ (3 eq), cat. DMAP, DCM, 4-6 hrs; ii) PhOCOCl (1.5 eq), NEt$_3$ (2.5 eq), DCM, 6 hrs; iii) TBAF (1 eq), THF, 1-2 hrs
OVERALL YIELDS 60-82%

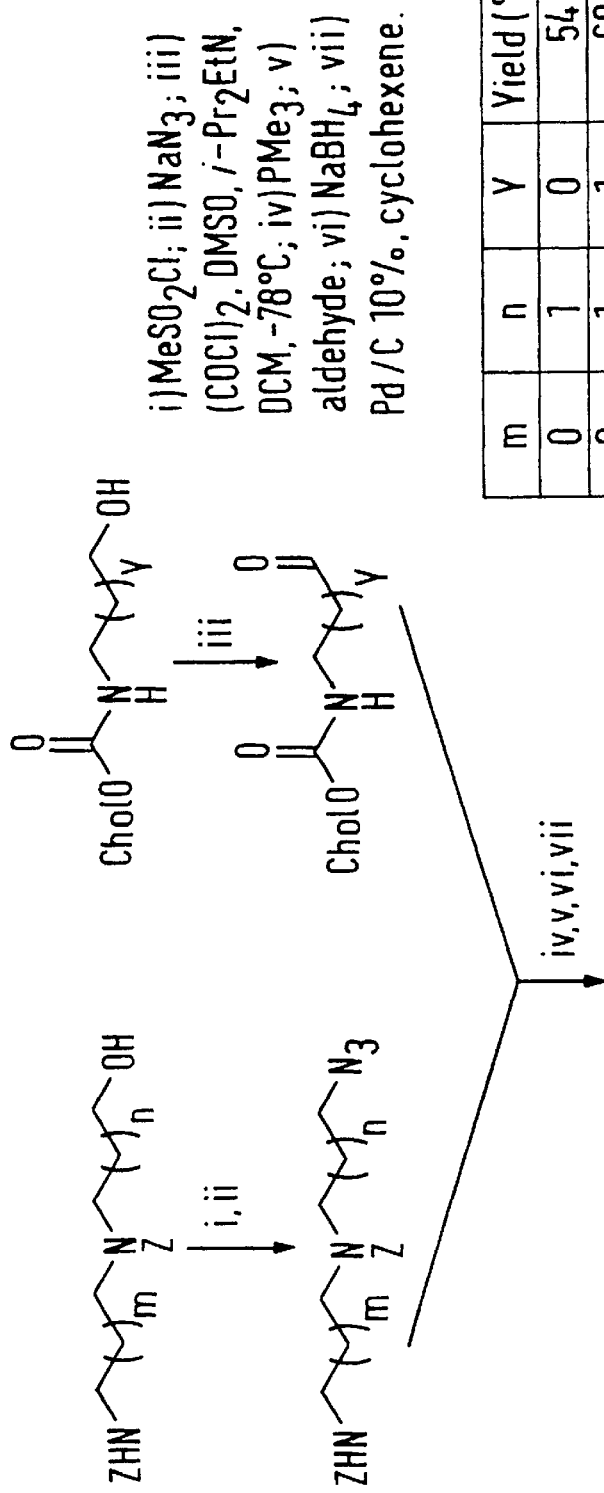
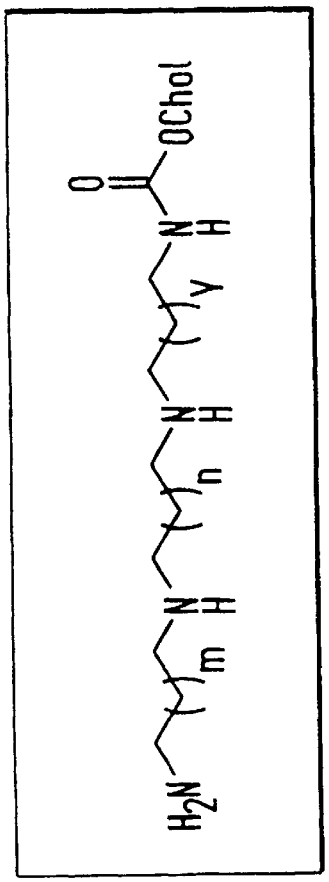
FIG. 20

APPLICATION TO SYNTHESIS OF PENTAMINOLIPIDS i) MeSO$_2$Cl; ii) NaN$_3$; iii) (COCl)$_2$, DMSO, i-Pr$_2$EtN, DCM, -78°C; iv) PMe$_3$; v) aldehyde; vi) NaBH$_4$; vii) Pd/C 10%, cyclohexene.

| m | n | x | y | Yield (%) |
|---|---|---|---|---|
| 1 | 2 | 2 | 1 | 56 |
| 0 | 1 | 2 | 1 | 74 |

FIG. 27 SCHEME B

FIG. 28 SCHEME C

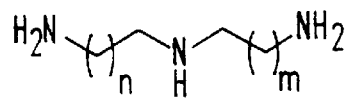
18' n = 3; m = 2
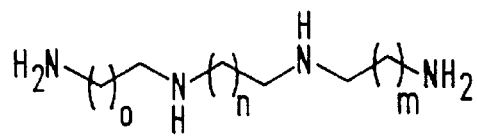
19' o = 2; n = 3; m = 2
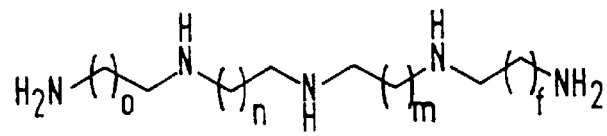
20' f, m, n, o = 2
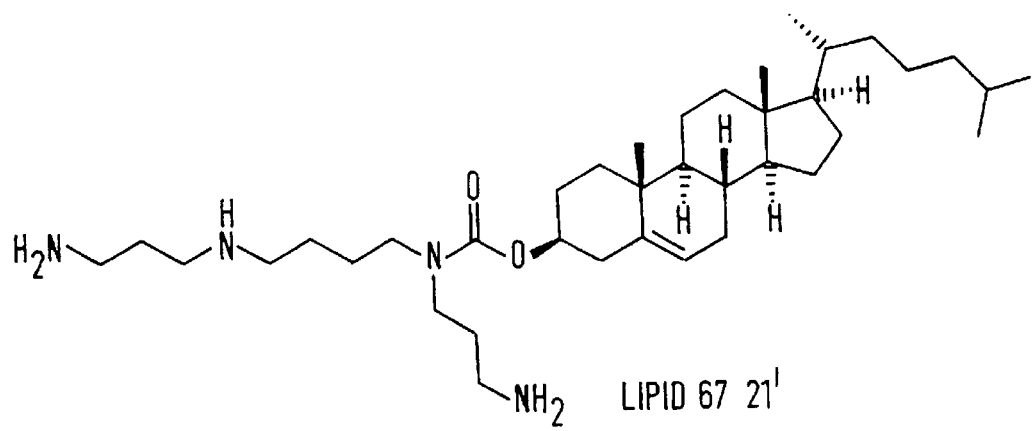
LIPID 67 21'
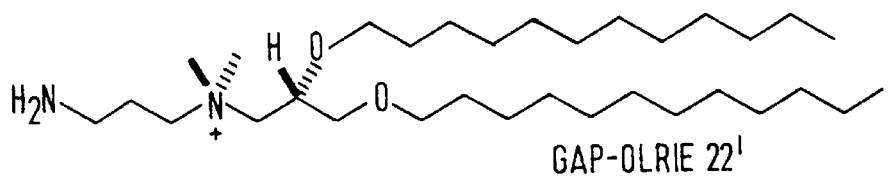
GAP-OLRIE 22'
FIG. 29

POLYCATIONIC STEROL DERIVATIVES AS TRANSFECTION AGENTS

The present invention relates to a compound. In addition, the present invention relates to processes for making the compound and to the use of that compound in therapy, in particular gene therapy (especially gene transfer).

One aspect of gene therapy involves the introduction of foreign nucleic acid (such as DNA) into cells, so that its expressed protein may carry out a desired therapeutic function.[1]

Examples of this type of therapy include the insertion of TK, TSG or ILG genes to treat cancer; the insertion of the CFTR gene to treat cystic fibrosis; the insertion of NGF, TH or LDL genes to treat neurodegenerative and cardiovascular disorders; the insertion of the IL-1 antagonist gene to treat rheumatoid arthritis; the insertion of HIV antigens and the TK gene to treat AIDS and CMV infections; the insertion of antigens and cytokines to act as vaccines; and the insertion of β-globin to treat haemoglobinopathic conditions, such as thalassaemias.

Many current gene therapy studies utilise adenoviral gene vectors—such as Ad3 or Ad5—or other gene vectors. However, serious problems have been associated with their use.[2] This has prompted the development of less hazardous, non-viral approaches to gene transfer.[3]

A non-viral transfer system of great potential involves the use of cationic liposomes.[4] In this regard, cationic liposomes—which usually consist of a neutral phospholipid and a cationic lipid—have been used to transfer DNA[4], mRNA[5], antisense oligonucleotides[6], proteins[7], and drugs[8] into cells. A number of cationic liposomes are commercially available[4,9] and many new cationic lipids have recently been synthesised[10]. The efficacy of these liposomes has been illustrated by both in vitro[4] and in vivo[11].

A neutral phospholipid useful in the preparation of a cationic liposome is N-[1-(2,3-dioleoyloxy)propyl]-N,N,N-trimethyl ammonium chloride, otherwise known as "DOTMA". The structure of DOTMA is shown in FIG. 1.

Figure 2:
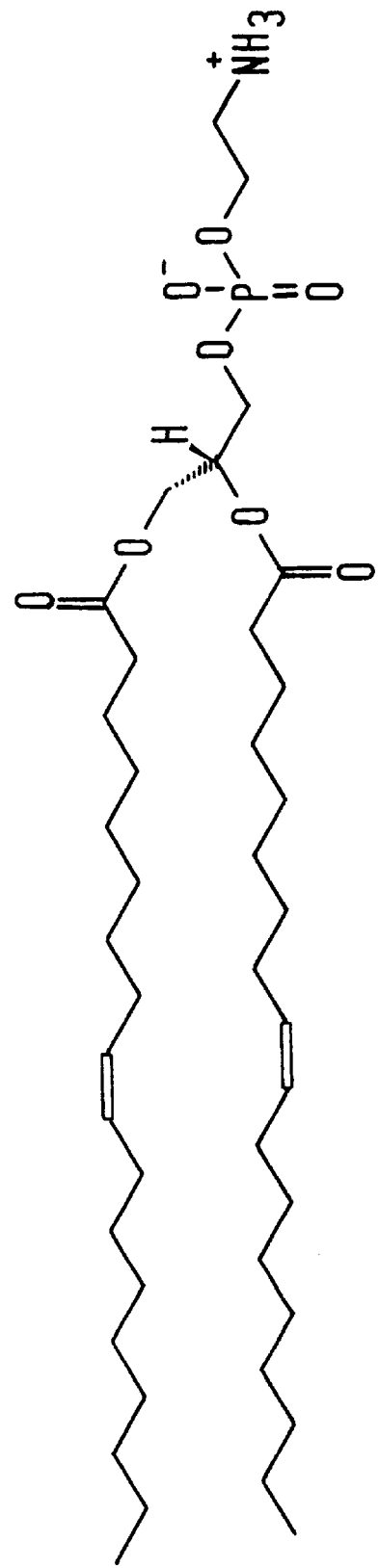
Figure 3:
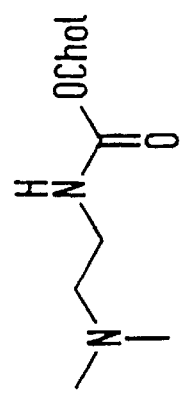

One of the most commonly used cationic liposome systems consists of a mixture of a neutral phospholipid dioleoylphosphatidylethanolamine (commonly known as "DOPE") and a cationic lipid, 3β-[(N,N-dimethylaminoethyl)carbamoyl]cholesterol (commonly known as "DC-Chol")[12]. The structure of DOPE is shown in FIG. 2. The structure of DC-Chol is shown in FIG. 3.

A lipid has been synthesised by reacting spermidine and cholesterol chloroformate in $CH_2Cl_2$ in the presence of N,N-diisoprophylethylamine[18]. However, this resulted in a mixture of the lipid and the corresponding regio-isomeric lipid, which mixture proved inseparable by chromatography.

Despite the efficacy of the known cationic liposomes there is still a need to optimise the gene transfer efficiency of cationic liposomes in human gene therapy[10].

According to one aspect of the present invention there is provided a compound capable of acting as a cationic lipid, the compound comprising a cholesterol group having linked thereto a head group; and wherein the head group is more positive than the head group of DC-Chol; but wherein the compound is not synthesised by reacting spermidine and cholesterol chloroformate in $CH_2Cl_2$ in the presence of N,N-diisoprophylethylamine.

As indicated above, the head group of DC-Chol is $Me_2N(CH_2)_2NH—$.

According to another aspect of the present invention there is provided a process of preparing a compound according to the present invention comprising reacting a cholesterol group with a head group.

According to another aspect of the present invention there is provided a compound according to the present invention or a compound when prepared by the process of the present invention for use in therapy.

According to another aspect of the present invention there is provided the use of a compound according to the present invention or a compound when prepared by the process of the present invention in the manufacture of a medicament for the treatment of a genetic disorder or a condition or a disease.

According to another aspect of the present invention there is provided a cationic liposome formed from the compound according to the present invention or a compound when prepared by the process of the present invention.

According to another aspect of the present invention there is provided a method of preparing a cationic liposome comprising forming the cationic liposome from the compound according to the present invention or a compound when prepared by the process of the present invention.

According to another aspect of the present invention there is provided a cationic liposome according to the present invention or a cationic liposome as prepared by the method of the present invention for use in therapy.

According to another aspect of the present invention there is provided the use of a cationic liposome according to the present invention or a cationic liposome as prepared by the method of the present invention in the manufacture of a medicament for the treatment of genetic disorder or condition or disease.

According to another aspect of the present invention there is provided a combination of a nucleotide sequence and any one or more of: a compound according to the present invention, a compound when prepared by the process of the present invention, a liposome of the present invention, or a liposome as prepared by the method of the present invention.

According to another aspect of the present invention there is provided a combination according to the present invention for use in therapy.

According to another aspect of the present invention there is provided the use of a combination according to the present invention in the manufacture of a medicament for the treatment of genetic disorder or condition or disease.

According to another aspect of the present invention there is provided a pharmaceutical composition comprising a compound according to the present invention or a compound when prepared by the process of the present invention admixed with a pharmaceutical and, optionally, admixed with a pharmaceutically acceptable diluent, carrier or excipient.

According to another aspect of the present invention there is provided a pharmaceutical composition comprising a cationic liposome according to the present invention or a cationic liposome as prepared by the method of the present invention admixed with a pharmaceutical and, optionally, admixed with a pharmaceutically acceptable diluent, carrier or excipient.

It is believed that a key advantage of the compound of the present invention is that it can be used as a cationic lipid (amphiphile) in the preparation of a cationic liposome useful in gene therapy, in particular the transfer of nucleic acids (including genes and antisense DNA/RNA) into cells (in vitro and in vivo) to derive a therapeutic benefit.

The cholesterol group can be cholesterol or a derivative thereof. Examples of cholesterol derivatives include substituted derivatives wherein one or more of the cyclic $CH_2$ or CH groups and/or one or more of the straight-chain $CH_2$ or CH groups is/are appropriately substituted. Alternatively, or in addition, one or more of the cyclic groups and/or one or more of the straight-chain groups may be unsaturated.

In a preferred embodiment the cholesterol group is cholesterol. It is believed that cholesterol is advantageous as it stabilises the resultant liposomal bilayer.

Preferably the cholesterol group is linked to the head group via a carbamoyl linkage. It is believed that this linkage is advantageous as the resultant liposome has a low or minimal cytotoxicity.

Preferably the head group is a polyamine group. It is believed that the polyamine group is advantageous because it increases the DNA binding ability and efficiency of gene transfer of the resultant liposome.

In one embodiment, preferably the polyamine group is a naturally occurring polyamine. It is believed that the polyamine head-group is advantageous because the increased amino functionality increases the overall positive charge of the liposome. In addition, polyamines are known to both strongly bind and stabilise DNA[14]. In addition, polyamines occur naturally in cells and so it is believed that toxicological problems are minimised[15].

Figure 4:
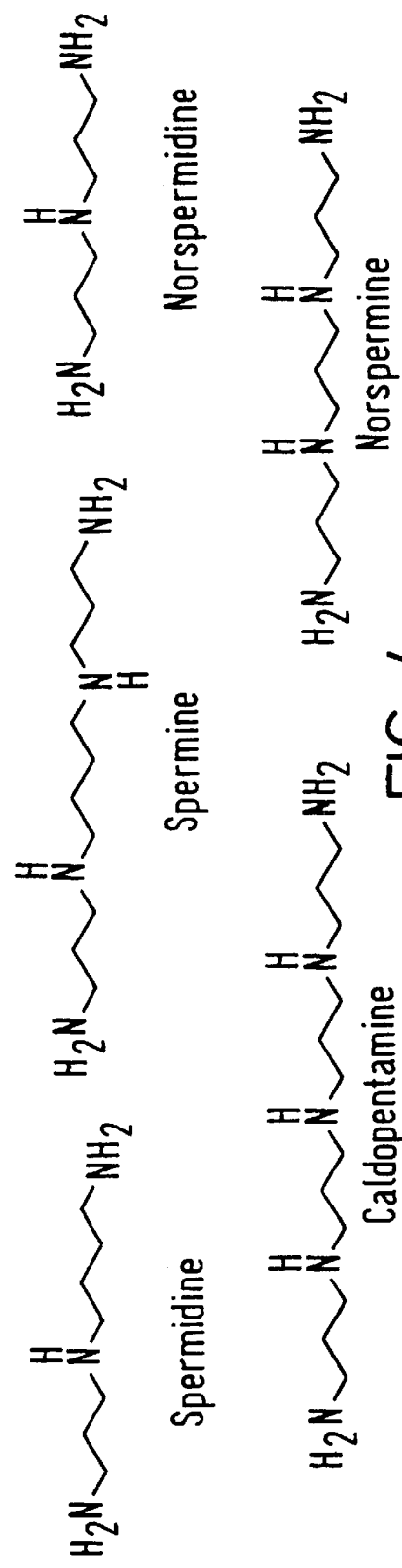

Typical examples of suitable polyamines include spermidine, spermine, caldopentamine, norspermidine and norspermine. These polyamines are shown in FIG. 4.

Preferably the polyamine is spermidine or spermine as these polyamines are known to interact with single or double stranded DNA. An alternative preferred polyamine is caldopentamine.

Figure 5:
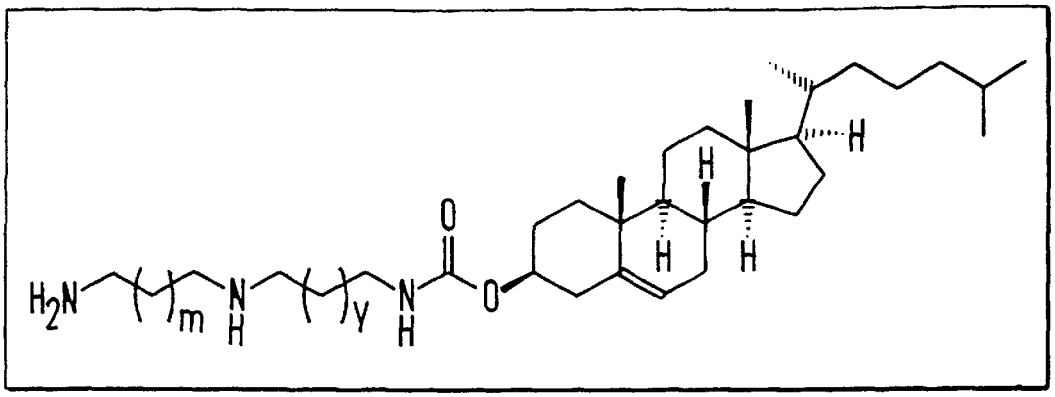

Thus, a preferred compound is spermidine linked to cholesterol via a carbamate linkage. This compound is shown in FIG. 5. It is believed that the polyamino head group is advantageous for DNA condensation, the carbamate linkage is stable but biodegradable and the cholesteryl group imparts bilayer rigidity. The carbamate linkage may be part of, or an integral component of, the head group.

Another preferred compound is spermine linked to cholesterol via a carbamate linkage. Likewise, it is believed that the polyamino head group is advantageous for DNA condensation, the carbamate linkage is stable but biodegradable and the cholesteryl group imparts bilayer rigidity.

Preferably the compound is in admixture with or associated with a nucleotide sequence.

The nucleotide sequence may be part or all of an expression system that may be useful in therapy, such as gene therapy.

Preferably the process comprises at least one step utilising aza-Wittig methodology.

Preferably the process comprises the use of trimethylphosphine.

Preferably the process comprises the use of a molecular sieve.

Preferably, the cationic liposome is formed from the compound of the present invention and a neutral phospholipid—such as DOTMA or DOPE. Preferably, the neutral phospholipid is DOPE.

In another embodiment, preferably two or more of the amine groups of the polyamine group of the present invention are separated by one or more groups which are not found in nature that separate amine groups of naturally occuring polyamine compounds (i.e. preferably the polyamine group of the present invention has un-natural spacing).

In summation, the present invention provides a compound capable of acting as a cationic lipid, the compound comprising a cholesterol group having linked thereto a head group; and wherein the head group is more positive than the head group of DC-Chol; but wherein the compound is not synthesised by reacting spermidine and cholesterol chloroformate in $CH_2Cl_2$ in the presence of N,N-diisoprophylethylamine.

A preferred embodiment of the present invention is a compound capable of acting as a cationic lipid, the compound comprising a cholesterol group having linked thereto a head group; wherein the head group is more positive than the head group of DC-Chol; wherein the cholesterol group is cholesterol; and wherein the head group is a polyamine group; but wherein the compound is not synthesised by reacting spermidine and cholesterol chloroformate in $CH_2Cl_2$ in the presence of N,N-diisoprophylethylamine.

A more preferred embodiment of the present invention is a compound capable of acting as a cationic lipid, the compound comprising a cholesterol group having linked thereto a head group; wherein the head group is more positive than the head group of DC-Chol; wherein the cholesterol group is cholesterol; wherein the head group is a polyamine group; and wherein the cholesterol group is linked to the head group via a carbamoyl linkage; but wherein the compound is not synthesised by reacting spermidine and cholesterol chloroformate in $CH_2Cl_2$ in the presence of N,N-diisoprophylethylamine.

A highly preferred embodiment of the present invention is a compound capable of acting as a cationic lipid, the compound comprising a cholesterol group having linked thereto a head group; wherein the head group is more positive than the head group of DC-Chol; wherein the cholesterol group is cholesterol; wherein the head group is a polyamine group; wherein the cholesterol group is linked to the head group via a carbamoyl linkage, and wherein the polyamine group is a naturally occurring polyamine, such as any one of spermidine, spermine or caldopentamine; but wherein the compound is not synthesised by reacting spermidine and cholesterol chloroformate in $CH_2Cl_2$ in the presence of N,N-diisoprophylethylamine.

Figure 6:
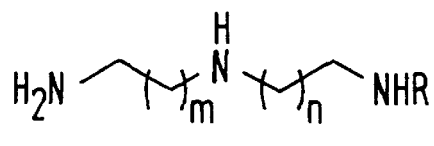
Figure 7:
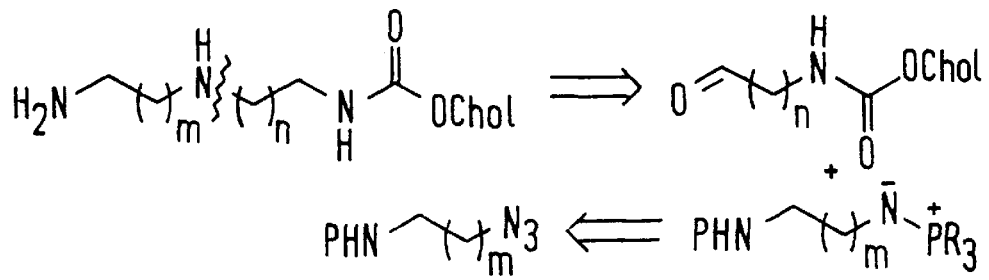
Figure 8:
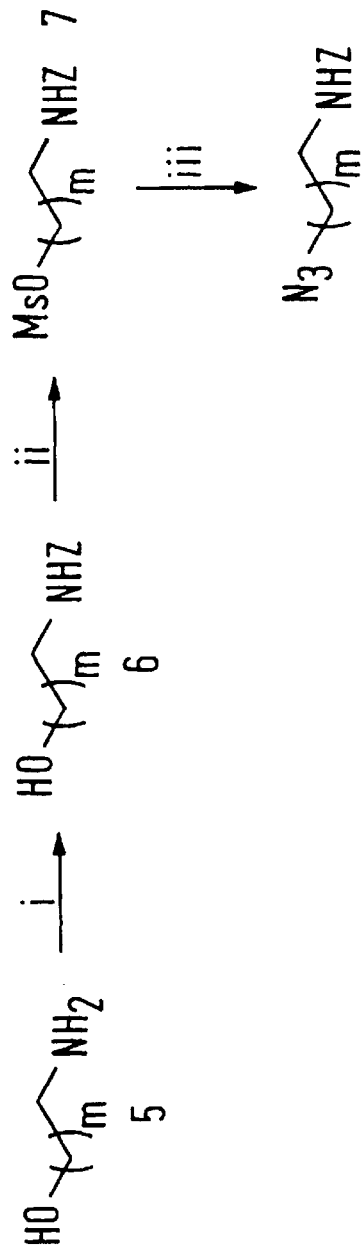
Figure 9:
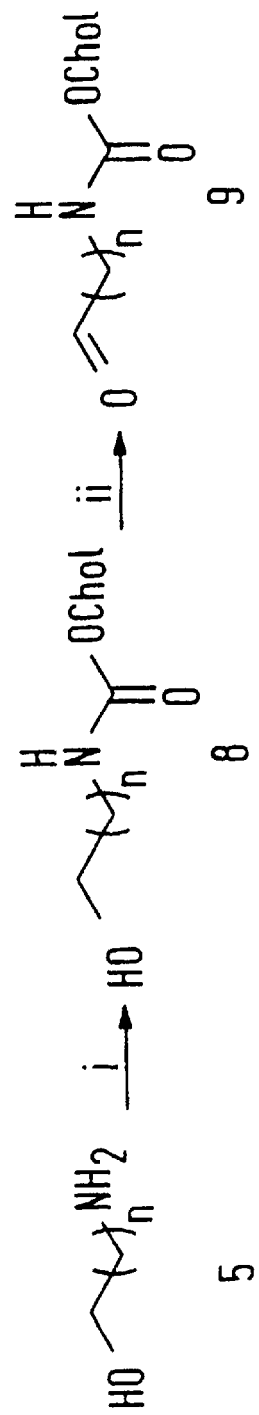
Figure 10:
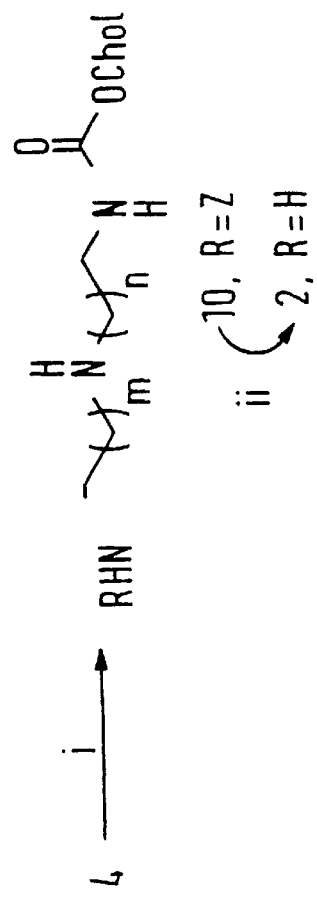
Figure 11:
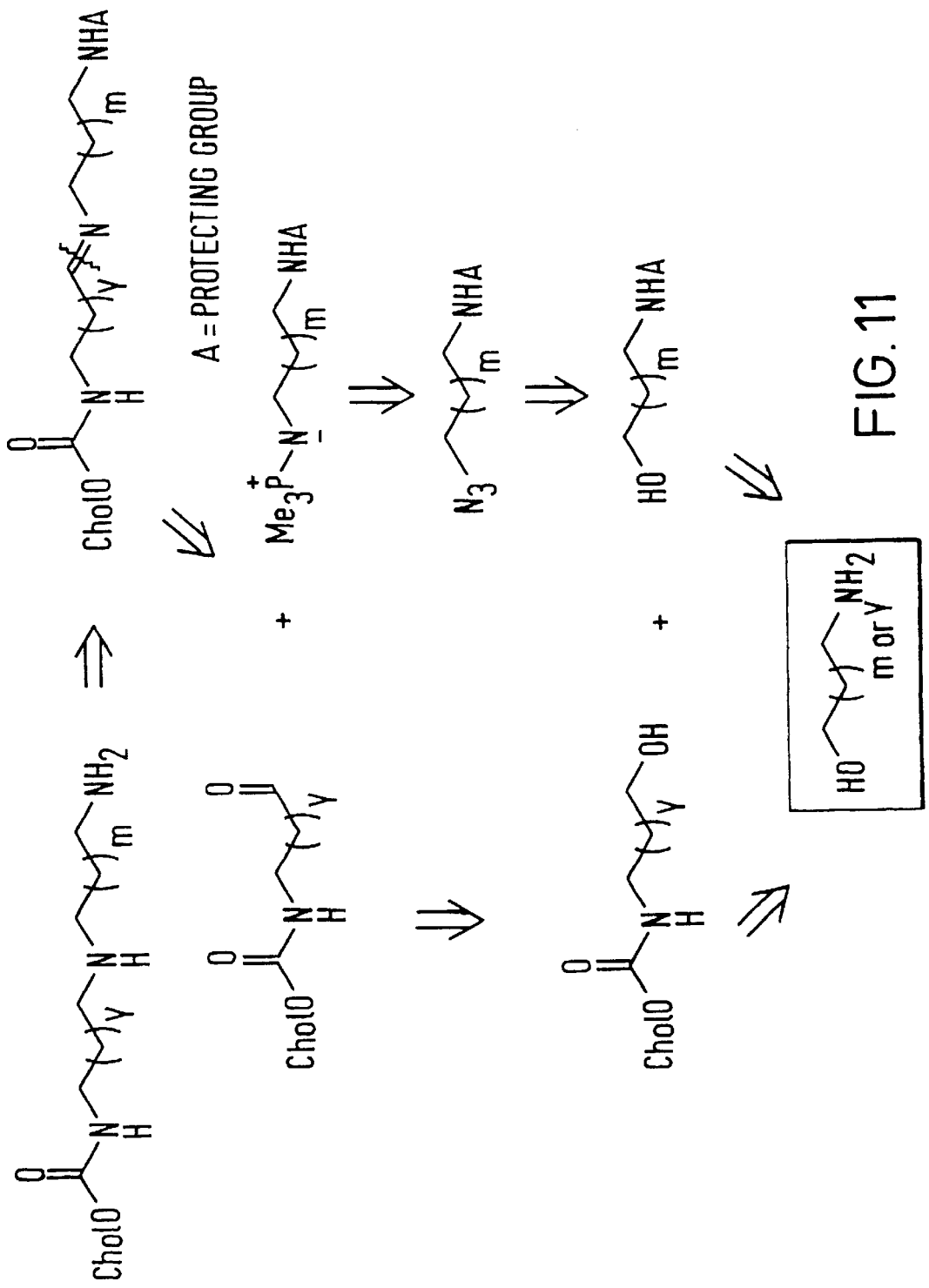
Figure 12:
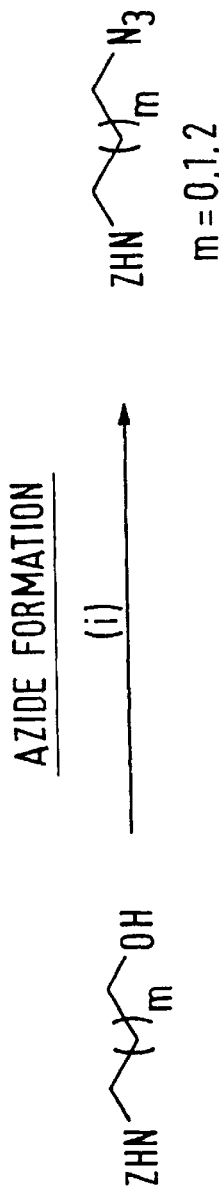
Figure 13:
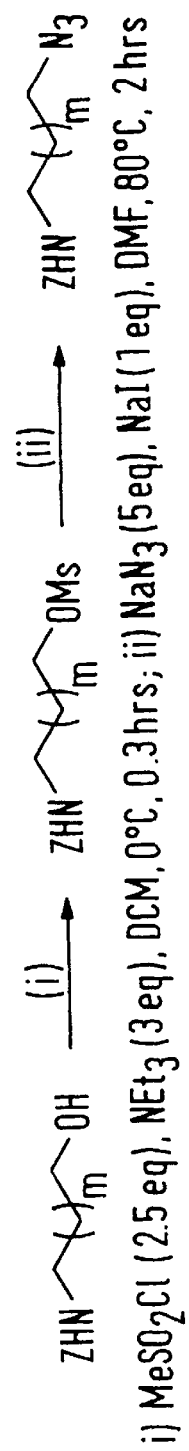
Figure 14:
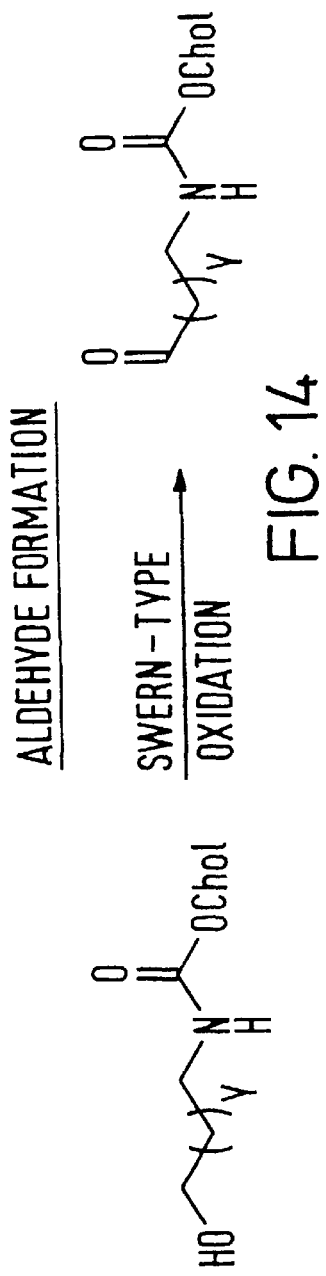
Figure 15:
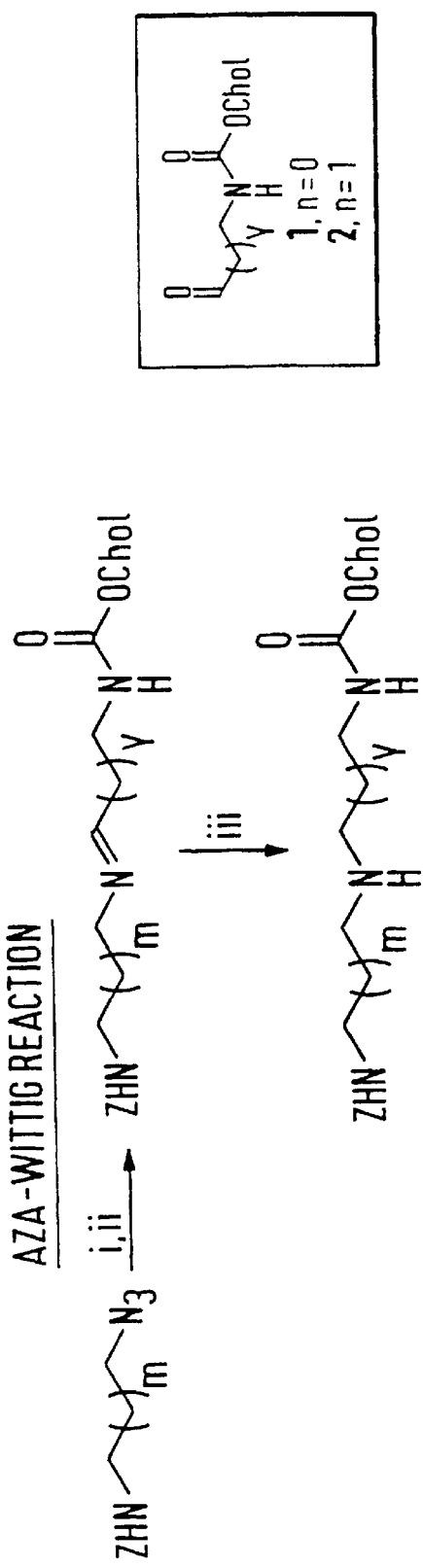
Figure 16:
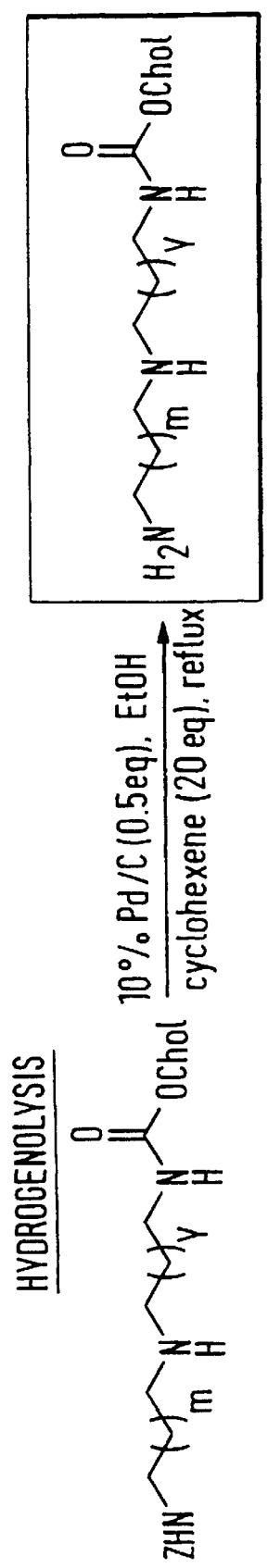
Figure 17:
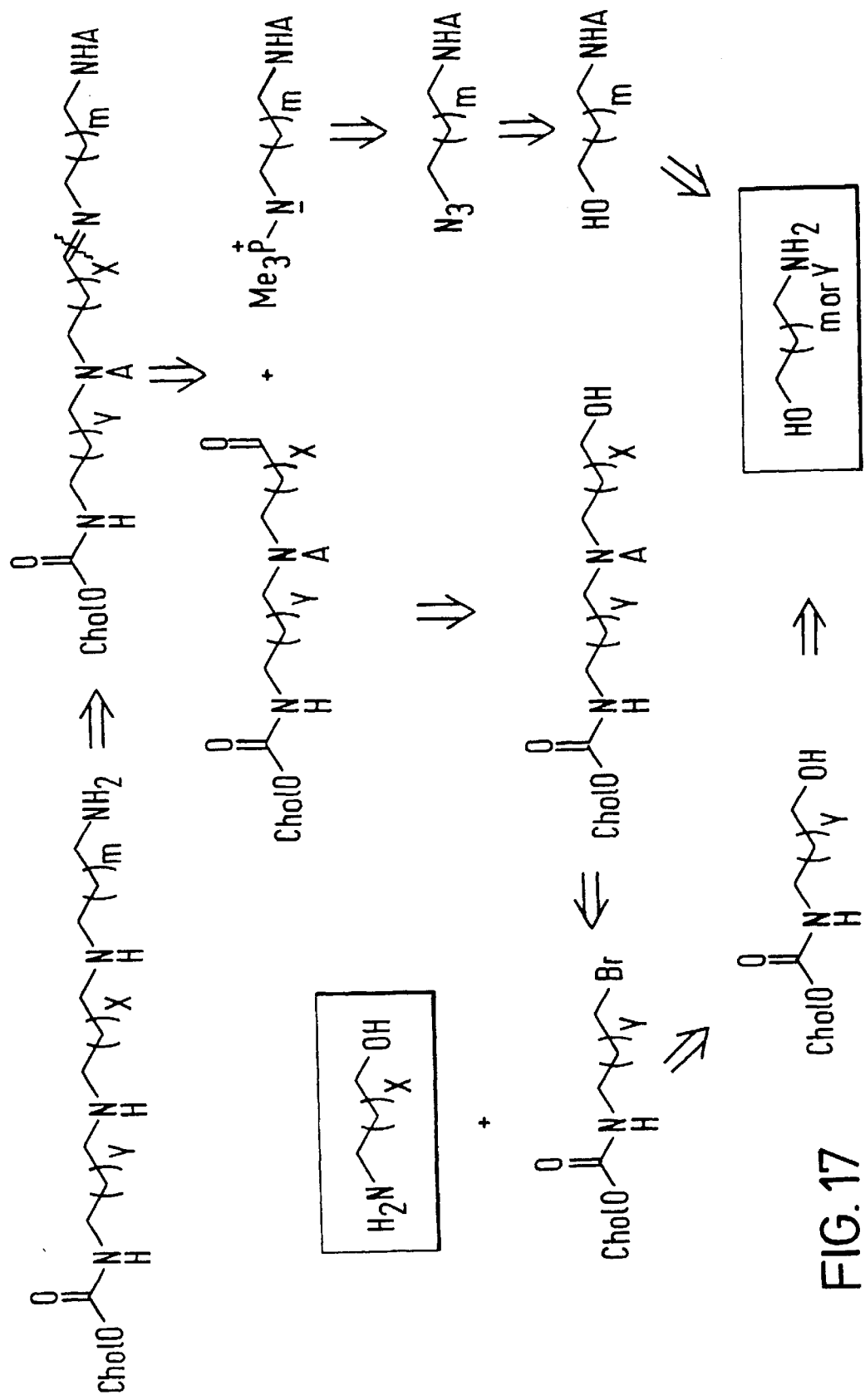
Figure 18:
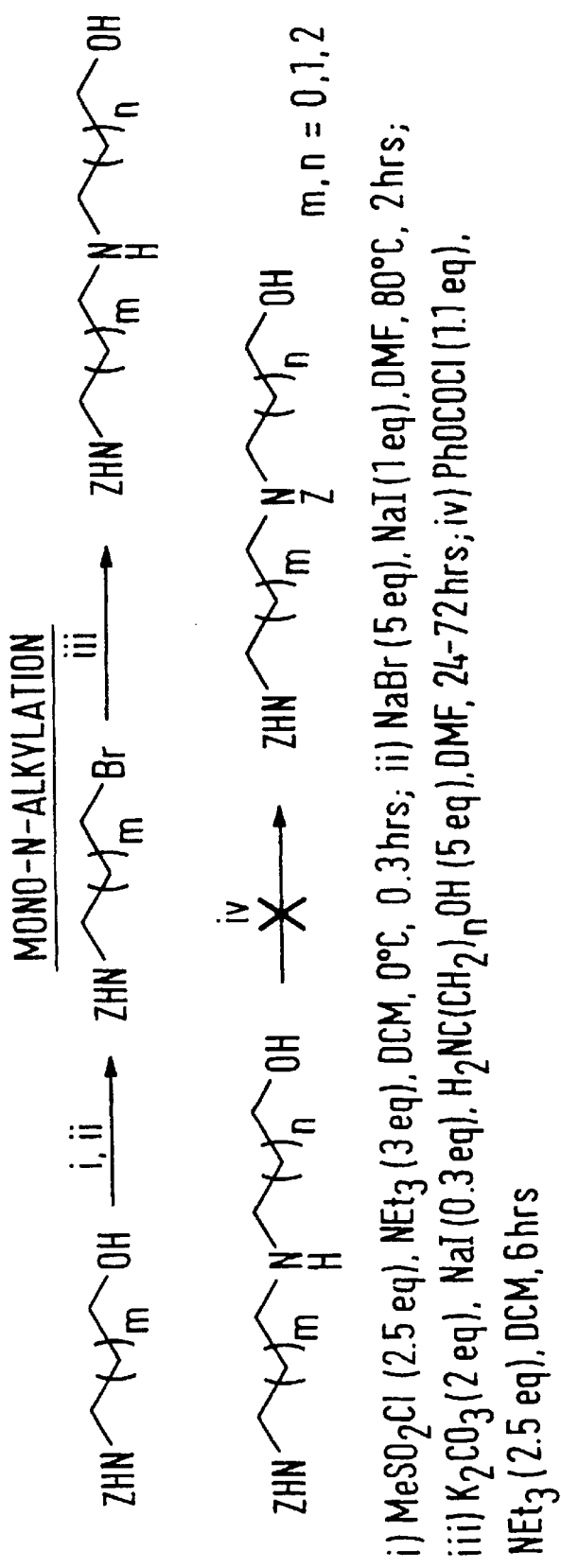
Figure 19:
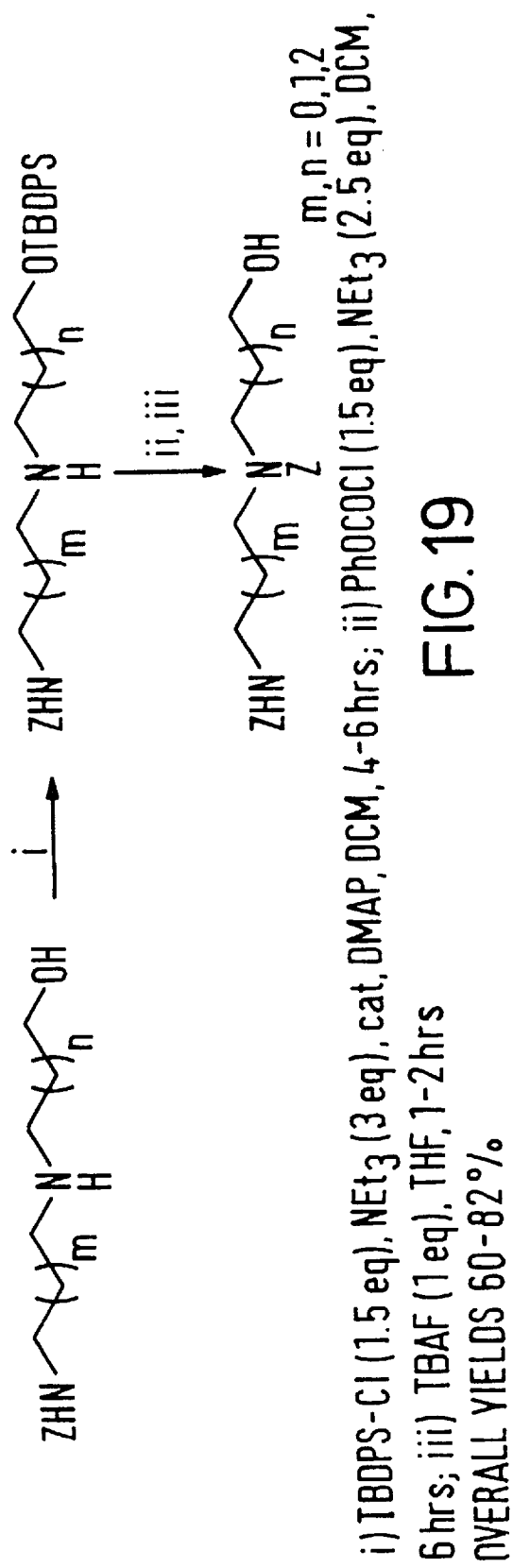
Figure 21:
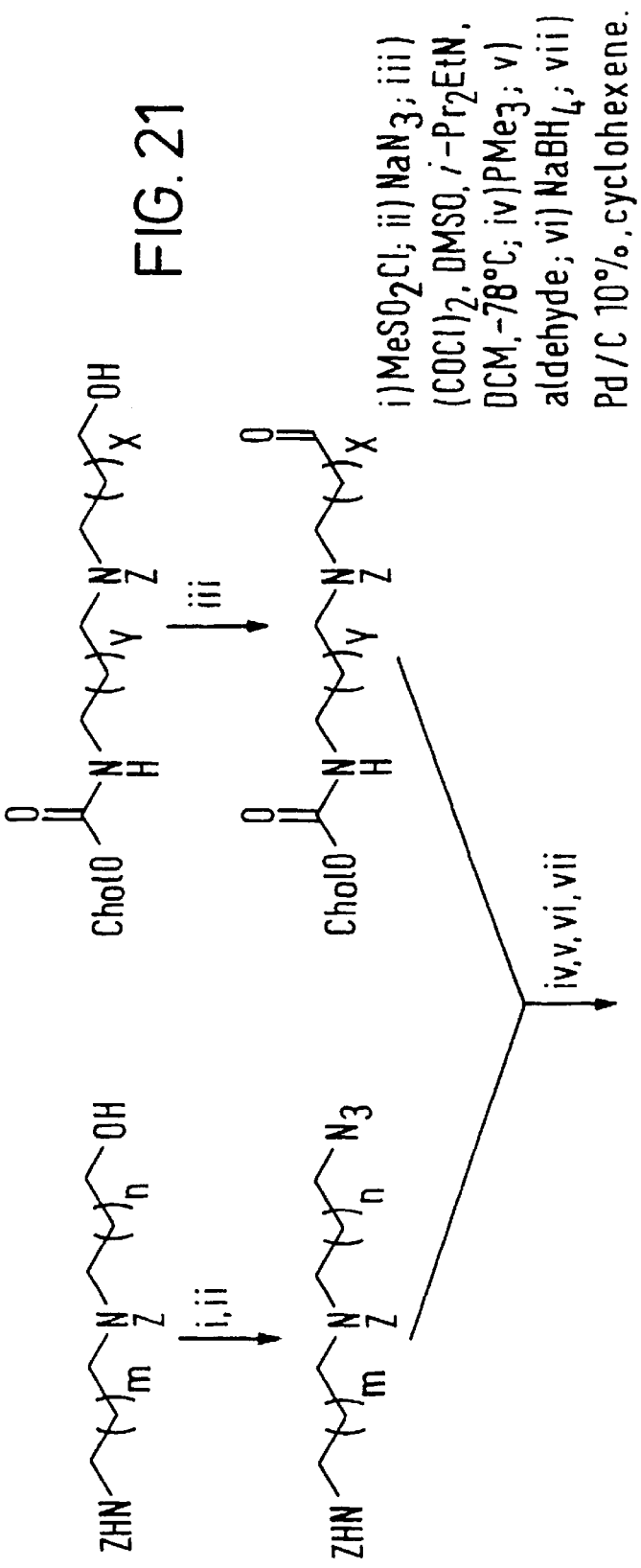
Figure 22:
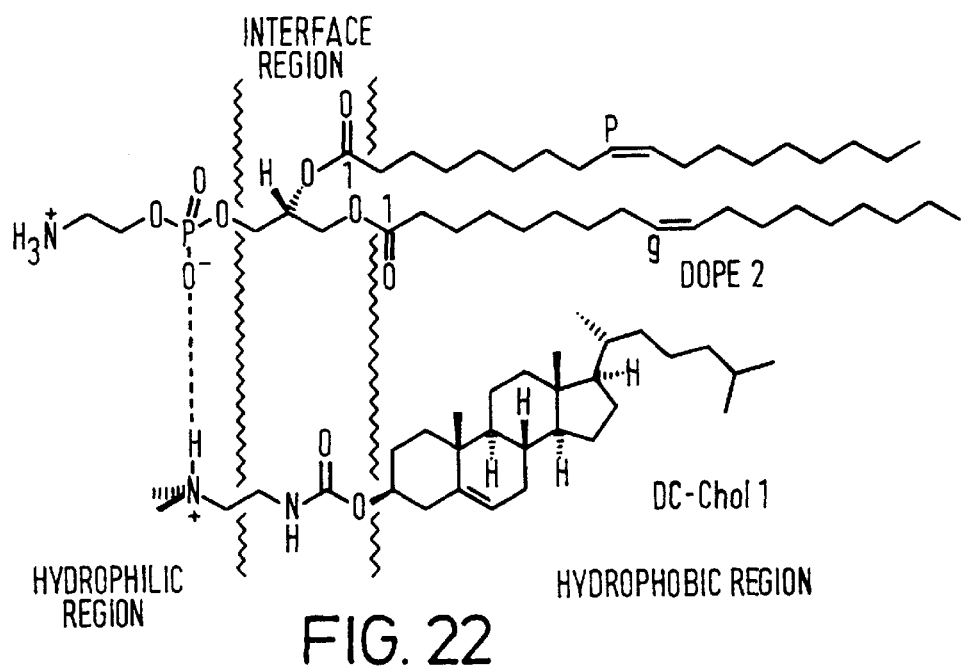
Figure 23:
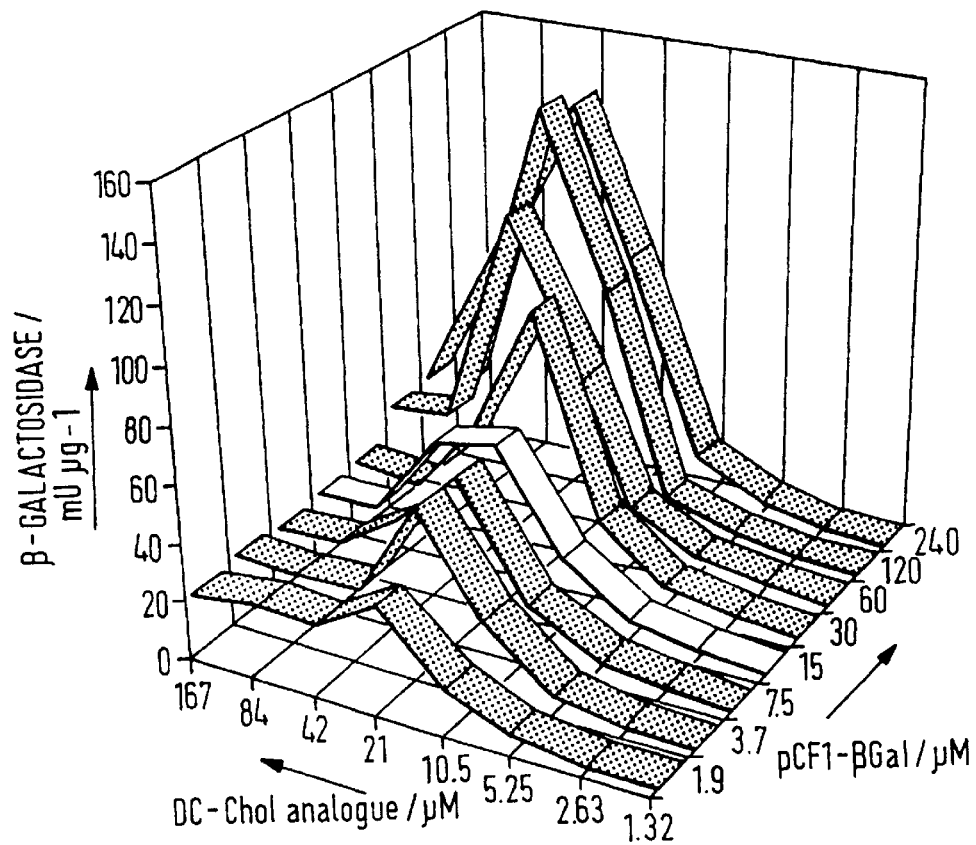
Figure 24:
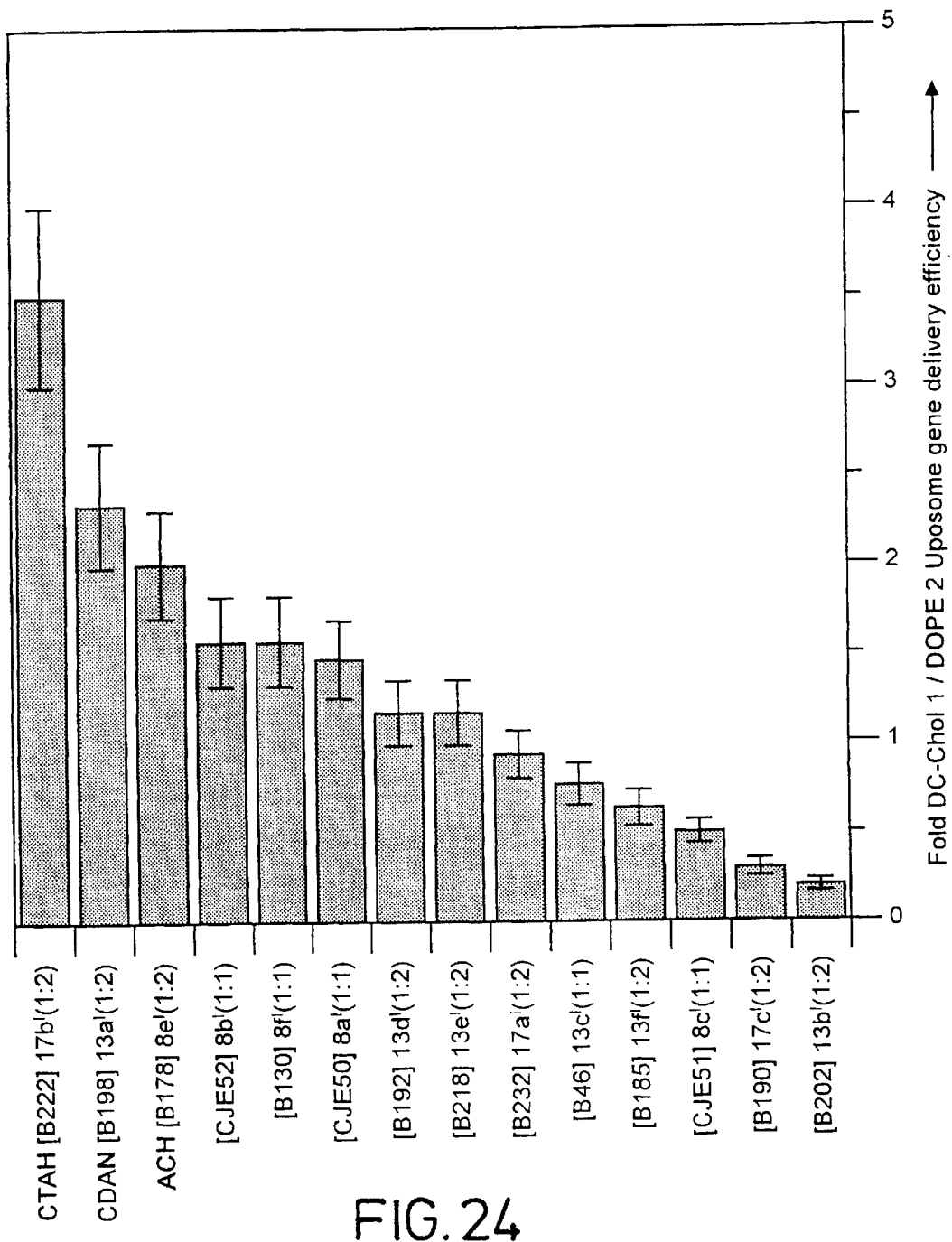
Figure 25:
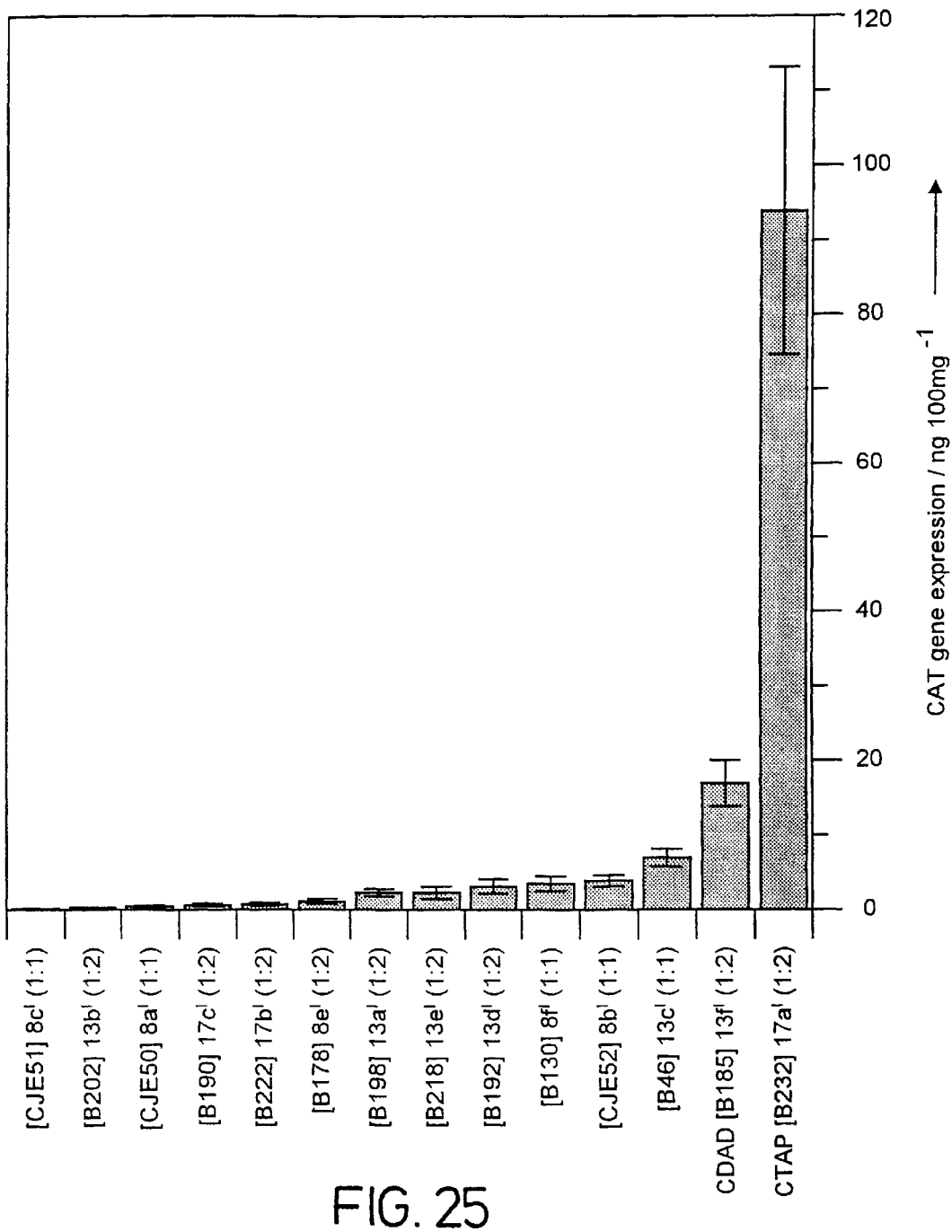
Figure 26:
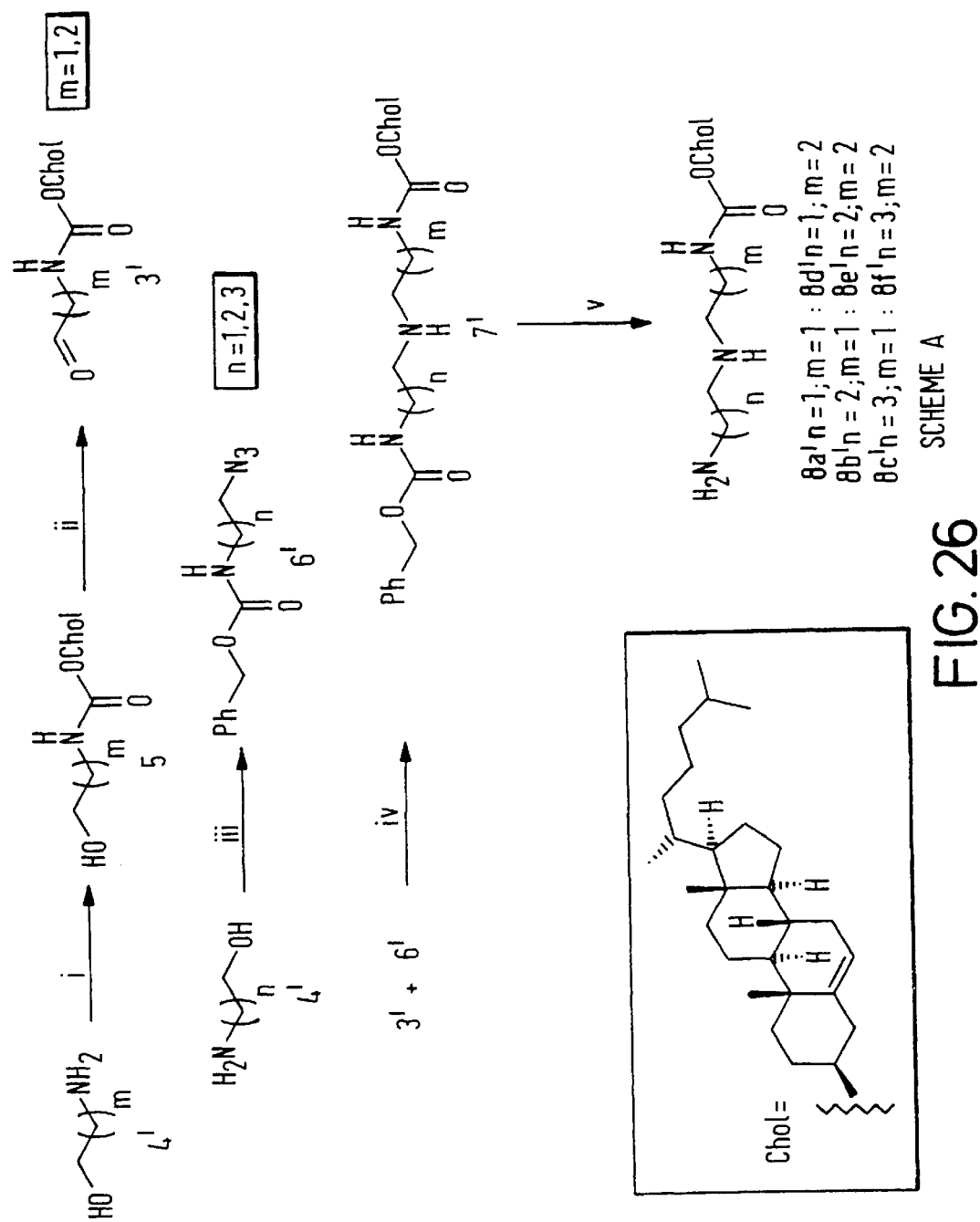
Figure 27:
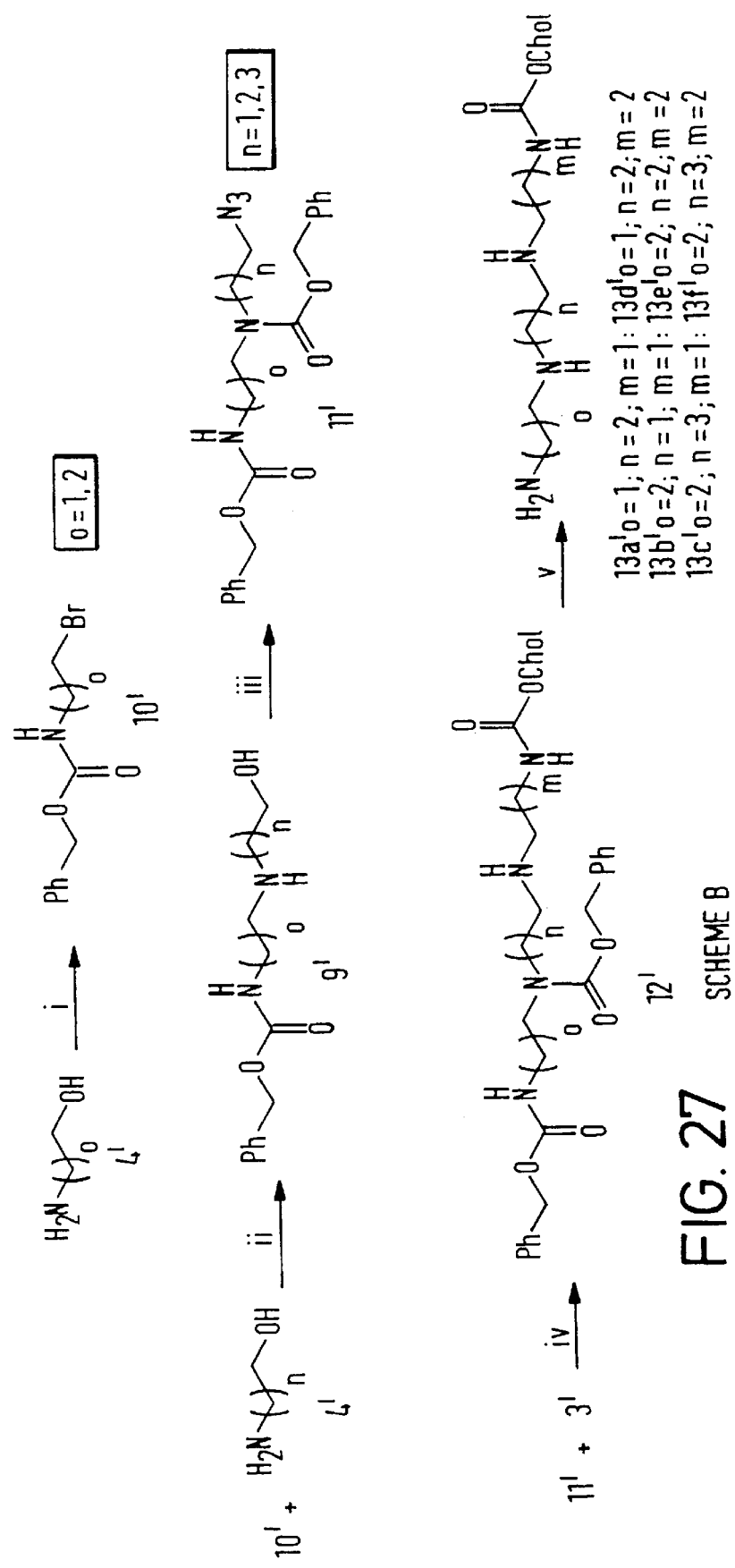
Figure 28:
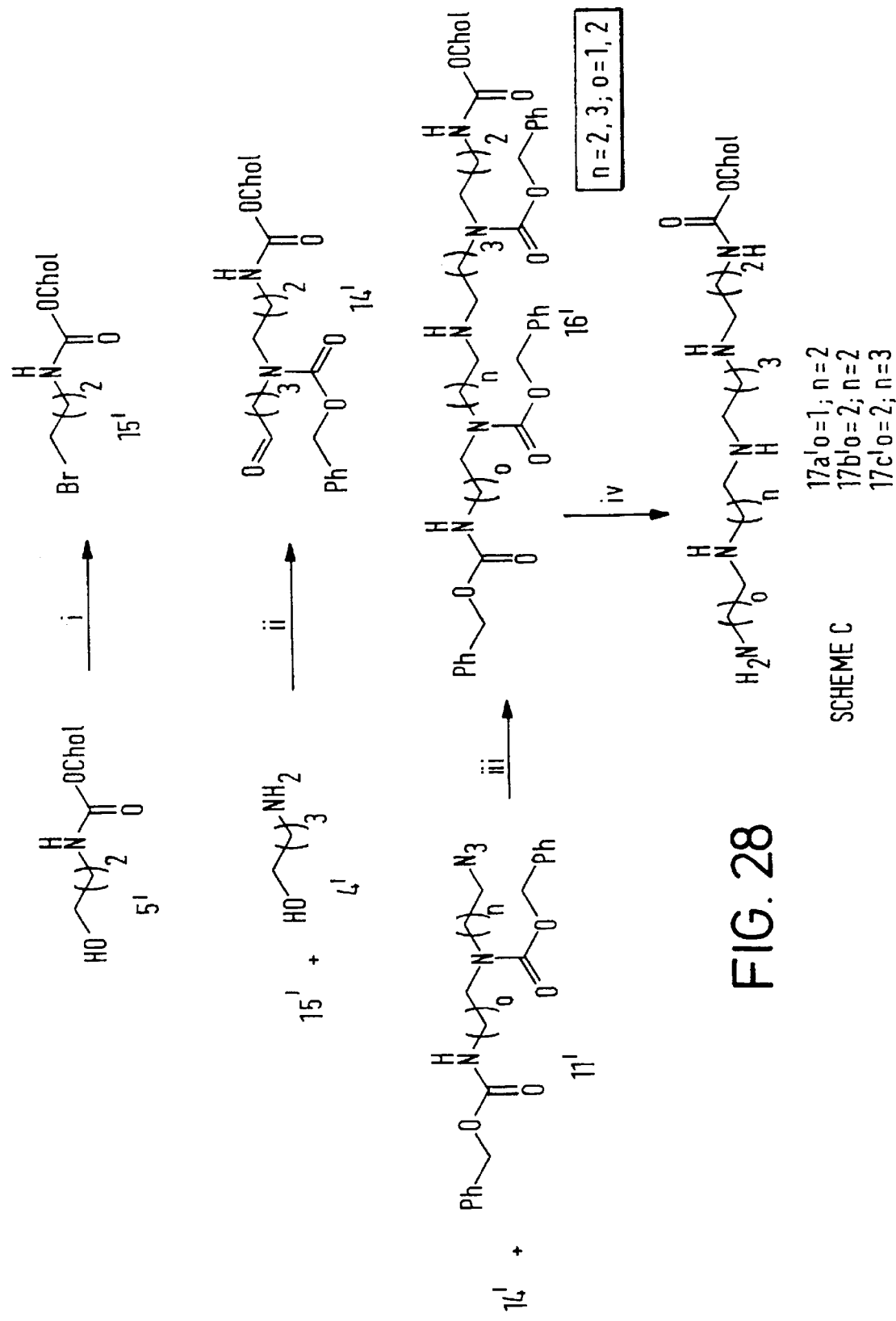

The present invention will now be described only by way of examples, in which reference is made to the following Figures:

FIG. 1 which is a structure;
FIG. 2 which is a structure;
FIG. 3 which is a structure;
FIG. 4 which is a series of structures;
FIG. 5 which is a structure;
FIG. 6 which is a structure;
FIG. 7 which includes a reaction scheme;
FIG. 8 which includes a reaction scheme and a Table of results;
FIG. 9 which includes a reaction scheme and a Table of results;
FIG. 10 which includes a reaction scheme and a Table of results;
FIG. 11 which includes a reaction scheme;
FIG. 12 which includes a reaction scheme and a Table of results;
FIG. 13 which includes a reaction scheme and a Table of results;
FIG. 14 which includes a reaction scheme and a Table of results;
FIG. 15 which includes a reaction scheme and a Table of results;
FIG. 16 which includes a reaction scheme and a Table of results;
FIG. 17 which includes a reaction scheme;
FIG. 18 which includes a reaction scheme and a series of results;

FIG. 19 which includes a reaction scheme and a series of results;

FIG. 20 which includes a reaction scheme and a Table of results;

FIG. 21 which includes a reaction scheme and a Table of results;

FIG. 22 which presents a model;

FIG. 23 which presents data from some studies;

FIG. 24 which presents data from some studies;

FIG. 25 which presents data from some studies;

FIG. 26 which presents a reaction scheme;

FIG. 27 which presents a reaction scheme;

FIG. 28 which presents a reaction scheme; and

FIG. 29 which presents some formulae.

GENERAL COMMENTS

In these studies DC-Chol was used as a template for the synthesis of more efficient gene transfer lipids, due to its good gene transfer ability[12] and low cytotoxicity[13]. In particular, the head group of DC-Chol was changed to a series of polyamine head-groups.

Initial Studies

Initially, a range of cationic lipids as shown in FIG. 6 (where m=1–3, n=1–2; referenced as 2), with head groups based on the naturally occurring polyamine, spernidine (m=3, n=3; referenced as 3) were synthesised.

To prepare these compounds we used aza-Wittig methodology[16], and so we made and used a range of suitably protected homologous azides and aldehydes (see Scheme 1 in FIG. 7).

Our initial studies suggested that benzyloxycarbonyl protected aminoazides (see FIG. 8, referenced as 4) would be suitable. These could be prepared in three steps and in excellent yield from aminoalcohols (see FIG. 8, referenced as 3), by sequential N-benzyloxycarbonylation, mesylation and azidation.

This process and the yields therefrom are shown in FIG. 8 (see Scheme 2 and Table 1).

The desired aldehyde could also be synthesised from aminoalcohols (see FIG. 9, referenced as 5) in excellent yield, this time by N-protection with cholesteryl chloroformate to give alcohols (see FIG. 9, referenced as 8), followed by Swern-type oxidation[17] to aldehydes (see FIG. 9, referenced as 9).

This process and the yields therefrom are shown in FIG. 9 (see Scheme 3, Table 2).

The aldehydes (9) were isolated as white crystalline solids which, in contrast with analogous aldehydes with different protecting groups, proved to be extremely stable, easy to handle and could be stored for long periods of time without any discernible decomposition.

The aza-Wittig reaction between azides (4) and aldehydes (9) occurred smoothly in THF to yield, after in situ reduction, protected polyamines (10) in excellent yield. We found that the use of trimethylphosphine rather than triphenylphosphine, led both to higher yields and lower reaction times. The use of molecular sieves also proved advantageous in obtaining consistently good yields, by eliminating adventitious water from the reaction system. Finally, removal of the benzyloxycarbonyl protecting group by hydrogenolysis yielded the desired lipids (2) in quantitative yield. These processes and the yields are shown in FIG. 10 (see Scheme 4, Table 3).

Liposomes containing the new lipids could be prepared using the following general procedure which by way of example refers to lipid (2) and DOPE.

Lipid (2) (6 μmol) and DOPE (298 μl of a 10 mg/ml solution in $CHCl_3$, 4 μmol) were added via syringe to freshly distilled $CH_2Cl_2$ (5 ml) under a nitrogen atmosphere. 4-(2-Hydroxyethyl)-1-piperazineethanesulfonic acid (HEPES) buffer (5 ml of a 20 mM solution adjusted to pH 7.8) was added. The two phase mixture was sonicated for 3 minutes and the organic solvents were removed under reduced pressure. The resulting liposome suspension was then sonicated for a further 30 min, yielding liposomes with an average diameter of 150 nm (as determined using a Coulter N4 MD photon correlation spectrometer).

The new compounds yielded the correct analytical data by $^1H$ NMR, $^{13}C$ NMR, 1R, MS and elemental analyses or HRMS.

This process therefore yields spermidine containing DC-Chol analogues from readily available starting materials, using aza-Wittig methodology. For these studies reference can also be made to FIGS. 11–21.

Further Studies

The further studies involved the inclusion of higher homologue polyamines such as spermine and unusual polyamines such as caldopentamine into a lipid framework. It is believed that these lipids, when used within the confines of a liposome, provide a DNA-condensing property that results in stronger, more stable liposome/DNA conjugates. Thus, we believe that these properties will improve the overall transfection of, for example, plasmid DNA into, for example, cell lines.

For these further studies reference can also be made to FIGS. 11–21.

Preparation of Methanesulfonate Esters

To a solution of dry alcohol (1.48 mmol) in dry $CH_2Cl_2$ (15 ml) was added triethylamine (0.62 ml, 4.4 mmol) and the solution stirred under nitrogen and cooled to around 0° C. At this point, methanesulfonyl chloride (0.29 ml, 3.7 mmol) in dry $CH_2Cl_2$ (5 ml) was added carefully and dropwise to the solution of alcohol. After the addition stirring was continued at 0° C. for 10 minutes and then at RT for 10 minutes. Ice was then added carefully and the reaction quenched for 35 minutes. The $CH_2Cl_2$ was diluted five-fold and then extracted with sat. ammonium chloride (70 ml), water (50 ml) and brine (70 ml). The organic layer was then dried over anhydrous sodium sulfate and the solvent removed in vacuo to give a quantitative yield of the crude mesylate.

Preparation of Azides

To a stirred mixture of methanesulfonate ester (1.48 mmol), sodium azide (0.48 g, 7.4 mmol, 5 eq.) and sodium iodide (0.222 g, 1.48 mmol) under $N_2$, was added by syringe dry DMF (10 ml) and the suspension heated to 80° C. This was maintained for two hours, and then allowed to cool to room temperature. The slurry was then filtered over Celite™ and the DMF removed under high vacuum to give a pale yellow oil.

The pale yellow oil was then redissolved in diethylether (100 ml) and washed with water (3×60 ml) and brine (80 ml). The organic layer was dried over anhydrous $Na_2SO_4$ and evaporated in vacuo to give the colourless azide. The azide was then purified further by flash column chromatography (ether/acetone 4–30%) to give the pure azide.

Preparation of Bromides

To a mixture of methanesulfonate ester (1 mmol) and sodium bromide (0.515 g, 5 mmol, 5 eq.) was added dry DMF (10 ml) via syringe and the solution heated at 80° C. for two hours, and then allowed to cool to room temperature and the slurry filtered over Celite™, and the DMF removed in vacuo. The bromide was then redissolved in diethylether (50 ml) and washed with water (3×30 ml) and brine (50 ml). The organic extract was dried over anhydrous $Na_2SO_4$, and the solvent removed in vacuo to give a colourless oil. The bromide was then purified by flash column chromatography (diethylether 20%/petrol 80%→diethylether) to give pure bromide.

Mono-N-Alkylation With Bromides

To a stirred solution of bromide (1 mmol) and 4-amino-1-butanol (0.36 g, 4 mmol, 4 eq.) in anhydrous DMF (10 ml) under $N_2$, was added anhydrous $K_2CO_3$ (0.276 g, 2 mmol, 2 eq.) and sodium iodide (15 mg, 0.1 mmol, 0.1 eq.). The reaction was stirred for 72 hours at room temperature, until reaction complete. The DMF was evaporated in vacuo and dried exhaustively under high vacuum. The resulting oily solid was redissolved in $CH_2Cl_2$ (100 ml) and washed with water (4×50 ml).

The combined aqueous extracts were then washed with $CH_2Cl_2$ (40 ml) and the $CH_2Cl_2$ extracts dried over anhydrous $Na_2SO_4$. The $CH_2Cl_2$ was evaporated in vacuo to give a pale yellow oil.

Aza-Wittig Reaction

To a suspension of flame-dried 4 Å molecular sieves (500 mg) and toluene-dried azide (1.08 mmol) in anhydrous THF (9 ml) under a nitrogen atmosphere, was added dropwise a solution of trimethylphosphine (1.2 ml of a 1.0 M solution in THF, 1.19 mmol, 1.1 eq.) via syringe.

After stirring at room temperature for one hour, the aldehyde (1.19 mmol, 1.1 eq.) in THF (2 ml) was added dropwise via cannula and the reaction mixture stirred for 18 hours. At this point, the THF was evaporated under nitrogen, and the resulting slurry resuspended in dry ethanol (7 ml). To this solution was added sodium borohydride (4.32 ml of 0.5 M solution in diglyme, 2.16 mmol, 2 eq.) via syringe and the reaction stirred for a further 24 hours at room temperature.

After this, the suspension was filtered over a short pad of Celite™, and the diglyme removed in vacuo. Exhaustive drying prior to work up was carried out, and the resulting oil redissolved in $CH_2Cl_2$ (120 ml) and treated with sat. sodium bicarbonate (100 ml), water (120 ml) and brine (120 ml). The organic fraction was dried over anhydrous $Na_2SO_4$ and the solvent removed in vacito to give a pale yellow oil and the crude product purified by flash column chromatography.

Hydrogenolysis

To a solution of Z-protected lipid (0.52 mmol, 1 eq.) in ethanol (6 ml) was added cyclohexene (2.11 ml, 20.8 mmol, 40 eq.) followed by palladium on activated carbon (10%, 277 mg, 0.5 eq.) under nitrogen blanket. The solution was then refluxed under nitrogen and the reaction followed by TLC ($CH_2Cl_2$/MeOH/$NH_3$ 92:7:1).

After two hours, the catalyst was carefully filtered off under nitrogen, washed with fresh ethanol and the solvent evaporated in vacuo to give a white solid.

Preparation of Silanols

To a cooled, stirred solution of alcohol (0.93 mmol), triethylamine (0.39 ml, 2.8 mmol) and DMAP (11.4 mg, 0.093 mmol, 0.1 eq.) in dry $CH_2Cl_2$ (1.5 ml) was added dropwise a solution of tert-butylchlorodiphenylsilane (0.6 ml, 2.33 mmol, 2.5 eq.) in dry $CH_2Cl_2$ (1.5 ml). The solution was stirred at room temperature for three to five hours at which point $CH_2Cl_2$ (45 ml) was added to the reaction mixture and then extracted with sat. sodium bicarbonate (70 ml) and brine (70 ml).

The $CH_2Cl_2$ extracts were dried over anhydrous $Na_2SO_4$ and the solvent removed in vacuo to give a pale yellow oil. This was purified by flash column chromatography.

N-Protection of Aminosilanols

To an ice-cooled aminosilanol (0.85 mmol) and triethylamine (0.24 ml, 1.7 mmol, 2 eq.) in $CH_2Cl_2$ (4 ml) was added dropwise a solution of phenylmethoxycarbonyl chloride (0.26 ml, 1.7 mmol, 2 eq.) in $CH_2Cl_2$ (1 ml). The resulting solution was stirred at room temperature for 18 hours. The solution was then diluted with $CH_2Cl_2$ (30 ml), washed with saturated ammonium chloride (40 ml) and brine (40 ml). The $CH_2Cl_2$ extract was then dried over anhydrous sodium sulfate and evaporated to dryness in vacuo to give a pale yellow oil. The compound was purified by flash column chromatography.

Preparation of Aldehydes

To a stirred solution of ethanedioyl dichloride (0.80 ml, 9.3 mmol, 1.5 eq.) in $CH_2Cl_2$ (20 ml) at −78° C. under a nitrogen atmosphere was added a solution of DMSO (1.35 ml, 18.6 mmol, 3 eq.) in $CH_2C_2$ (20 ml) via cannula over a time period of 15 minutes. The resulting solution was stirred for a further 20 minutes after which time a solution of alcohol (6.2 mmol, 1 eq.) in $CH_2Cl_2$ (60 ml) was added dropwise via cannula. After a further 30 minutes N,N,N-diisopropylethylamine (3.25 ml, 18.6 mmol, 3 eq.) was added dropwise and the solution warmed slowly to room temperature.

The pale yellow solution was then washed with saturated ammonium chloride (150 ml), saturated sodium bicarbonate (80 ml) and water (100 ml). The aqueous extracts were combined and washed with $CH_2Cl_2$ (100 ml). The $CH_2Cl_2$ extracts were combined, washed with brine (100 ml) and dried over anhydrous sodium sulfate. The solvent was then evaporated in vacuo to give a pale yellow solid. The crude aldehyde was then purified by flash column chromatography (ether) to a white solid.

Deprotection of Silanols

To a solution of silanol (1 mmol) in THF (5 mmol) was added carefully tetrabutyl ammonium fluoride (TBAF) (1.1 mmol) and the solution stirred for two to three hours. The solution was then diluted with $CH_2Cl_2$ (50 ml) and sat. sodium bicarbonate (50 ml) added. The organic phase was collected, washed with water (50 ml) and brine (60 ml). The organic layer was then dried over anhydrous sodium sulfate, and the solvent removed in vacuo. The pale yellow oil was then purified by flash column chromatography.

Additional Studies

For these particular studies reference is made inter alia to FIGS. 22–28.

In particular, FIG. 22 is the putative alignment of DC-Chol 1 and DOPE 2 in cationic liposome bilayer.

FIG. 23 is an example of in vitro optimisation of pCF1-βGal plasmid transfection of CFT1 cells in vitro using complexes of pCF1-βGal and cationic liposomes formulated from DC-Chol analogue 8f' and DOPE 2 (1:1) molar ratio. CFT1 cells were transfected with an array of different cationic liposome and plasmid ratios in a 96-well plate. The extent of transfection in each well was determined after 2 days by measuring the levels of β-galactosidase expression. Plasmid DNA concentration is expressed as the concentration of nucleotides assuming an average nucleotide FWt of 330. Cationic liposome concentration is expressed in terms of the concentration of the constituent DC-Chol analogue 8f' alone.

FIG. 24 presents rank order of DC-Chol polyamine analogues transfecting CFT1 cells in vitro with the pCF1-βGal plasmid. Gene delivery activity is expressed as a proportion of the activity measured with standard liposomes containing DC-Chol 1 and DOPE 2. The data shown are the averages of four separate experiments, each performed in triplicate.

The ratios in curved brackets refer to the DC-Chol analogue:DOPE 2 molar ratio used to formulate the liposomes. The numbers in square brackets refer to compound serial numbers. Where appropiate DC-Chol analogue name abbreviations are also included (see experimental).

FIG. 25 presents the rank order of DC-Chol polyamine analogues transfecting the lungs of female BALB/c mice with the pCF1-CAT plasmid. Mice were instilled with a solution of the plasmid (4 mM nucleotide concentration) and the optimal quantity and ratio of cationic liposome, in a total volume of 100 μl. Gene delivery activity was determined as a function of chloramphenicol acetyl transferase activity in lung homogenates after 2 days.

Data points were from separate experiments with each optimal formulation tested in 4 BALB/c mice. The ratios in curved brackets refer to the DC-Chol analogue:DOPE 2 molar ratio. The numbers in square brackets refer to compound serial numbers. Where appropiate DC-Chol analogue name abbreviations are also included (see experimental).

Extra studies have shown that the gene delivery efficiency of DC-Chol/DOPE liposomes is equivalent to the performance of liposomes containing DC-Chol analogue 8c'.[32]

In order to improve to DC-Chol/DOPE liposomes, a simple model for the association of DC-Chol 1 and DOPE 2 in the bilayer of a cationic liposome was devised (FIG. 22). This was based upon the proposed behaviour of cholesterol in bilayer membranes[26] and a liposome model proposed by Felgner and co-workers.[27]

Carbon atoms C-1 to C-9 of the oleoyl side chains of DOPE 2 pack against the four fused cholesterol rings of DC-Chol 1 so that the phosphate ester group of DOPE and the protonated tertiary amine functionality of DC-Chol 2 are aligned and neutralise each other. The positive charge of the liposome then derives from the protonated ethanolamine side chain of DOPE 2. On the basis of the recent transfection experiments in mouse and human[24, 25] it was thought that increased transfection efficiency could best be achieved by constructing either DC-Chol or DOPE polyamine analogues which would be expected to interact with DNA more strongly. Since DOPE is sensitive to oxidation of the oleoyl cis- double bonds, we considered that it would be more appropriate to synthesise polyamine analogues of DC-Chol instead. The model (FIG. 22) suggested that the methylene group spacing between carbamoyl and the first amine functional group of a given DC-Chol polyamine analogue should be two or at most three, in order to maintain charge complementation with DOPE 2. The prefered DC-Chol polyamine analogues (i.e. polyamine analogues of 3DF-[N-(N',N'-dimethylaminoethane) carbamoyl]cholesterol) were designed with this constraint in mind.

The syntheses of triamine analogues of DC-Chol were carried out as follows.

Initially, two different N-cholesteryloxycarbonylaminoaldehydes 3' were prepared by N-protection of aminoalcohols 4' with cholesteryl chloroformate followed by Swern-type oxidation[28] of protected alcohols 5' to give the aldehydes 3' (see Scheme A in FIG. 26). Typically speaking aminoaldehydes can be quite unstable and prone to polymerisation but the steric stabilisation of the N-cholesteryl moiety resulted in crystalline compounds which could be stored for extended periods of time without any discernible decomposition.

N-Benzyloxycarbonyl protected aminoazides 6' were then prepared in three steps from aminoalcohols 4' using sequential N-benzyloxycarbonylation, mesylation and azidation (Scheme A). Finally, azides 6' were coupled to aminoaldehydes 3' using aza-Wittig methodology[29, 30] giving protected DC-Chol triamine analogues 7' which were stored at this stage. In our hands, aza-wittig coupling reactions were found to be more efficient with trimethylphosphine rather than the customary triphenylphosphine, in line with literature precedent.[29] Also, the elimination of adventitious water with activated molecular sieves proved helpful to obtain consistently high yields.[29] Just prior to any gene delivery studies, protecting groups were removed by catalytic transfer hydrogenolysis, to give triamine analogues 8' (Scheme A) in 44–77% overall yield.

The syntheses of tetramine analogues of DC-Chol were carried out in the following way. Several different N-protected diaminoalcohols 9' were prepared by mono N-alkylation of aminoalcohols 4' with N-benzyloxycarbonyl protected aminoalkylbromides 10'. Bromides 10' were themselves prepared in three steps from aminoalcohols by sequential N-benzyloxycarbonylation, mesylation and bromination (see Scheme B in FIG. 27). Customarily, mono-N-alkylations of primary amines are considered to be difficult to control. Nevertheless, a combination of steric crowding in the reactants and mild reaction conditions are now being found increasingly to prevent over-N-alkylation occuring.[31] Temporary protection of the alcohol functional groups of 9' as t-butyldiphenylsilylethers, followed by N-benzyloxycarbonylation and fluoride promoted desilylation gave bonafide di-N-benzyloxycarbonyl protected diaminoalcohols which were then converted into diaminoazides 11' by mesylation followed by azidation (Scheme B). Finally, protected DC-Chol tetramine analogues 12' were formed by coupling azides 11' to cholesteryl-aminoaldehydes 3' by means of the the aza-Wittig procedure once more (Scheme B). As for the preparation of 8' (Scheme A), protecting groups were removed just prior to transfection studies by catalytic transfer hydrogenolysis giving tetramine analogues 13' (Scheme B) in 12–38% overall yield. Gratifyingly, we found that the mono-N-alkylation procedure could be used equally well to prepare N-cholesteryloxycarbonyl-diaminoaldehyde 14' from N-cholesterylalcohol 5' via bromide 15' (see Scheme C in FIG. 28). As a result, several fully protected DC-Chol pentamine analogues 16' could be prepared by aza-Wittig coupling of diaminoaldehyde 14' to di-N-benzyloxycarbonyl protected diaminoazides 11'. DC-Chol pentamine analogues 17' were then prepared by hydrogenolysis of the protecting groups in the usual way (Scheme C).

The ability of cationic liposomes containing the different DC-Chol polyamine analogues to mediate gene delivery was analysed both in vitro and in vivo. Cationic liposomes were formulated by hydrating a dried lipid film, containing DC-Cholanalogue and DOPE 2 in an appropriate molar ratio of either 1:0, 1:1, 1:2 or 2:1 respectively. and vortex mixing.

[32] Cationic liposome/plasmid DNA complexes were then prepared by adding appropriately diluted cationic liposome suspensions into equal volumes of aqueous plasmid DNA solutions at 30° C. and allowing the mixture to equilibrate to ambient temperature over 15 min.[32] In vitro studies were then performed with immortalised cystic fibrosis airway epithelial (CFT1) cells followed by in vivo studies in which cationic liposome/plasmid DNA complexes were instilled intranasally into the lungs of female BALB/c mice.[32] Typically, cationic liposome gene delivery was first optimised in vitro so as to establish the best molar ratio of cationic liposome to plasmid DNA (DNA concentration was expressed as nucleotide concentration) as well as the best absolute quantities of both, as illustrated (FIG. 23). This optimised combination was then tested in vivo. The in vitro results are shown (FIG. 24). Six DC-Chol analogue containing liposomes proved to confer significant improvements on gene delivery efficiency over and above DC-Chol/DOPE liposomes formulated in a similar way. The analogues were 8a', 8b', 8e', 8f', 13a' and 17b', the first four being triamines, the fifth a tetramine and the sixth a pentamine. With one exception, 8f', these polyamine analogues contain inter-nitrogen methylene group spacings not normally associated with the natural polyamines spermidine 18' (see for example FIG. 29), spermine 19' (see for example FIG. 29) and pentamine 20' (see for example FIG. 29) upon which these structures are based. In vivo (FIG. 25), the best DC-Chol analogues were 13c', 13f' and especially 17a'. Both 17a' and 13c' also contain unnatural methylene group spacings.

Of the best in vivo analogues, 17a' works about 100-fold more effectively in mouse lung than DC-Chol 1 and approx 500-fold relative to plasmid DNA alone (FIG. 25). Only one other cytofectin has been reported to function at this level of efficacy in vivo, namely the lipid 67 21' (see FIG. 29), a "T" shaped tetramine analogue of DC-Chol.[32] None of the other reported cytofectins appear to be close to this level of in vivo efficacy with the possible exception of (B1)-N-(3-aminopropyl)-N,N-dimethyl-2,3-bis-(dodecyloxy)-1-propanaminium bromide (GAP-DLRIE) 22' (see FIG. 29) which has been reported to work about 100 fold better than plasmid DNA alone.[33] Other cytofectins have been reported, but frequently have either not yet been used in vivo or else with rather poor results.[21, 34, 35]

Analogues 8f' and 13f' have been reported previously, either without synthetic characterisation details[32] or else as impure mixtures known as SpdC and SpC respectively.[34] In the former case, in vitro and in vivo gene delivery behaviours were found to be comparable with our results reported here.[32] In the latter case, SpC was reported not to work well and to be relatively toxic.[34] Our data with analogue 13f' do not support these observations.

Experimental Procedure

The synthetic procedures used to make the DC-Chol polyamine analogues are documented below.

Scheme A

Reagents and conditions: i, $CH_2Cl_2$ (0.2M), CholOC(O)Cl (0.45 eqv), 5 h, 98–99%; ii, (a) $CH_2Cl_2$ (0.1M) $(COCl)_2$ (1.5 eqv), DMSO (3 eqv), −78° C., 15 min; (b) 5', 15 min; (c) i-$Pr_2$NEt (3 eqv) to r.t., 93–97%; iii, (a) $CH_2Cl_2$ (0.2M), $PhCH_2OC(O)Cl$ (0.45 eqv), 10 h; (b) $CH_2Cl_2$ (0.2M), $Et_3N$ (3 eqv), $CH_3SO_2Cl$ (2.5 eqv), 0° C. to r.t., 15 min; (c) DMF (0.15 M), $NaN_3$ (5 eqv), NaI, 80° C., 2 h, 68–87%; iv, (a) 6', THF (0.5 M), 4 Å molecular sieves, $PMe_3$ (1.15 eqv), 30 min; (b) 3' (1.1 eqv), 3h; (c) EtOH (0.5 M), $NaBH_4$ (2 eqv), 20 h, 72–90%; v, EtOH (0.2M), c-C6H10 (20 eqv), 10% Pd(C) (0.5 eqv), reflux, 30 min, 99%.

Scheme B

Reagents and conditions: i, (a) $CH_2Cl_2$ (0.2M), $PhCH_2OC(O)Cl$ (0.45 eqv), 10 h; (b) $CH_2Cl_2$ (0.2M), $Et_3N$ (3 eqv), $CH_3SO_2Cl$ (2.5 eqv), 0° C. to r.t., 15 min; (c) DMF (0.15 M), NaBr (5 eqv), 80° C., 2 h, 68–87%; ii, 10', DMF (0.1M), 4' (5 eqv), $K_2CO_3$ (2 eqv), NaI (0.3 eqv), 24–72 h, 74–88%; iii, (a) $CH_2Cl_2$ (0.2M), $Et_3N$ (1.5 eqv), TBDPSCl (1.2 eqv), DMAP (0.1 eqv), 09AC to r.t., 2–4 h; (b) $CH_2Cl_2$ (0.2M), $PhCH_2OC(O)Cl$ (1.5 eqv), $Et_3N$ (1.5 eqv), 6–10 h; (c) THF (0.5M), TBAF (1.1 eqv), 4–5 h; (d) $CH_2Cl_2$ (0.2M), $Et_3N$ (3 eqv), $CH_3SO_2Cl$ (2.5 eqv), 0° C. to r.t., 15 min; (e) DMF (0.15M), $NaN_3$ (5 eqv), NaI, 80° C., 2 h, 37–70%; iv, (a) 11', THF (0.5M), 4 Å molecular sieves, $PMe_3$ (1.15 eqv), 30 min; (b) 3' (1.1 eqv), 3 h; (c) EtOH (0.5M), $NaBH_4$ (2 eqv), 20 h, 64–71%; v, EtOH (0.2M), c-C6H10 (20 eqv), 10% Pd(C) (0.5 eqv), reflux, 30 min, 99%.

Scheme C

Reagents and conditions: i, (a) $CH_2Cl_2$ (0.2M), $Et_3N$ (3 eqv), $CH_3SO_2Cl$ (2.5 eqv), 0° C. to r.t., 15 min; (b) DMF (0.15 M), NaBr (5 eqv), 80° C., 2 h, 68–87%; ii, (a) 15', DMF (0.1M), 4' (5 eqv), $K_2CO_3$ (2 eqv), NaI (0.3 eqv), 24–72 h; (b) $CH_2Cl_2$ (0.2M), $Et_3N$ (1.5 eqv), TBDPSCl (1.2 eqv), DMAP (0.1 eqv), 0° C. to r.t., 2–4 h; (c) $CH_2Cl_2$ (0.2M), $PhCH_2OC(O)Cl$ (1.5 eqv), $Et_3N$ (1.5 eqv), 6–10 h; (d) THF (0.5M), TBAF (1.1 eqv), 4–5 h; (e) $CH_2Cl_2$ (0.1M) $(COCl)_2$ (1.5 eqv), DMSO (3 eqv), −78° C., 15 min; (f) di N-protected diaminoalcohol, 15 min; (g) i-$Pr_2$NEt (3 eqv) to r.t., 53–66%; iii (a) 11', THF (0.5M), 4 Å molecular sieves, $PMe_3$ (1.15 eqv), 30 min; (b) 14' (1.1 eqv), 3 h; (c) EtOH (0.5 M), $NaBH_4$ (2 eqv), 20 h, 56–74%; iv, EtOH (0.2M), c-C6H10 (20 eqv), 10% Pd(C) (0.5 eqv), reflux, 30 min, 99%.

Data

Representative analytical data presented for the most effective analogues in vitro (triamine 8e', tetramine 13a' and pentamine 17b') and in vivo (tetramine 13f' and pentamine 17a')

4-aza-N'-cholesteryloxycarbonyl-1,7-heptanediamine (ACH) [B178] 8e'

$v_{max}$ ($CH_2Cl$,) 3347, 2937, 2905, 2868, 1698, 1534, 1467, 1379 and 1264 cm$^{-1}$; $\delta_H$ (300 MHz) 5.76 (1H, br s, NHCO), 5.22 (1H, m, H-6'), 4.33 (1H, m, H-3'), 3.08 (2H, m, H-1), 2.65 (2H, t, J 6.5 Hz, H-7), 2.53 (2H, t, J 6.5 Hz, H-3), 2.41 (2H, m, H-5), 2.24–2.12 (2H, m, H-4'), 1.90–1.69 (5H, m, H-2', H-7', H-8') 1.55–0.93 (28H, m, H-2, H-4, H-6, H-1', H-9', H-11', H-12', H-14' to H-17', H-20', H-22' to H-25', NH$_2$), 0.88 (3H, s, H-19'), 0.79 (3H, d, J 6.5 Hz, H-21'), 0.73 (6H, dd, J 6.0 and 0.5 Hz, H-26' and H-27'), 0.55 (3H, s, H-18'); bc (75 MHz) 156.29 (NHC(O)O), 139.77 (C-5'), 122.24 (C-6'), 73.85 (C-3'), 56.59 (C-14'), 56.09 (C-17'), 49.92 (C-9'), 47.61 (C-1), 47.52 (C-3), 42.20 (C-4'), 40.22 (C-5), 39.66 (C-16'), 39.42 (C-24'), 38.57 (C-7), 36.94 (C-2), 36.44 (C-22'), 36.11 (C-8'), 35.71 (C-20'), 33.04 (C-7'), 31.78 (C-6), 28.14 (C-2'), 27.87 (C-25'), 24.19 (C-12'), 23.78 (C-15'), 22.74 (C-23'), 22.49 (C-26'), 20.96 (C-11'), 19.25 (C-19'), 18.65 (C-21'), 11.77 (C-18'); m/z (FAB) 544 (M+H)$^+$, 369 (Chol)$^+$, 95, 43 (Found: (M+H)$^+$, 544.4885. $C_{34}H_{62}N_3O_2$ requires (M+H)$^+$, 544.4842).

N'-cholesteryloxy-carbonyl-3,7-diaza-1,9-nonanediamine (CDAN) [B198] 13a'

$v_{max}$ (CH$_2$Cl$_2$) 3584–3245, 2937, 2868, 1695, 1538, 1469, 1379, 1251, 1133 and 1014 cm$^{-1}$; $\delta_H$ (400 MHz) 5.82 (1H, br s, NHCO), 5.23 (1H, m, H-6'), 4.33 (1H, m, H-3'), 3.54–2.55 (16H, m, H-1 to H-4, H-6 to H-9, H$_2$N), 2.21–2.09 (2H, m, H-4'), 1.97–1.73 (5H, m, H-2', H-7', H-8'), 1.55–0.99 (23H, m, H-5, H-1', H-9', H-11', H-12', H-14' to H-17', H-20', H-22' to H-25'), 0.88 (3H, s, H-19'), 0.78 (3H, d, J 6.0 Hz, H-21'), 0.74 (6H, d, J 6.5 Hz, H-26' and H-27'), 0.55 (3H, s, H-18'); $\delta_C$(100 MHz) 156.38 (NHC(O)O), 139.70 (C-5'), 122.30 (C-6'), 73.99 (C-3'), 56.56 (C-14'), 56.05 (C-17'), 51.91 (C-1), 49.88 (C-9'), 47.95 (C-2), 42.18 (C-4'), 41.12 (C-8), 39.63 (C-16'), 39.40 (C-24'), 38.53 (C-2), 36.90 (C-1'), 36.42 (C-22'), 36.08 (C-8'), 35.69 (C-20'), 31.75 (C-7'), 29.62 (C-5), 28.12 (C-2'), 27.86 (C-25'), 24.17 (C-12'), 23.75 (C-15'), 22.73 (C-23'), 22.48 (C-26'), 20.94 (C-11'), 19.24 (C-19'), 18.62 (C-21'), 11.76 (C-18'); m/z (FAB) 573 (M+H)$^+$, 544, 513, 460, 369 (Chol)$^+$, 215, 95 (Found: (M+H)$^+$, 573.5139. C$_{35}$H$_{65}$N$_4$O$_2$ requires (M+H)$^+$, 573.5108).

N$^{10}$-cholesteryloxycarbonyl-4,8,13-triaza-1,16-hexadecanediamine(CTAH)[B222] 17b'

$V_{max}$ (CH$_2$Cl$_2$) 3344. 2936, 2855, 1700, 1536, 1468, 1379, 1265, 1122 and 1028 cm$^{-1}$; $\delta_H$ (300 MHz) 5.69 (1H, br s, NHCO), 5.22 (1H, d, J 4.0 Hz, H-6'), 4.33 (1H, m, H-3'), 3.20 (2H, m, H-1), 2.63 (2H, t, J 6.5 Hz, H-3), 2.55–2.35 (12H, m, H-5, H-8, H-10, H-12, H-14, H-16), 2.23–2.08 (7H, m, H-4, H-9, H-13, H-4', NH$_2$), 1.90–1.63 (5H, m, H-2', H-7', H-8'), 1.57–0.90 (31H, m, H-2, H-6, H-7, H-11, H-15, H-1', H-9', H-11', H-12', H-14' to H-17', H-20', H-22' to H-25'), 0.87 (3H, s, H-19'), 0.78 (3H, d, J 6.5 Hz, H-21'), 0.73 (6H, d, J 6.5 Hz, H-26' and H-27'), 0.55 (3H, s, H-18'); $\delta_C$(75 MHz) 156.27 (NHC(O)O), 139.79 (C-S'), 122.24 (C-6'), 73.86 (C-3'), 56.58 (C-14'), 56.06 (C-17'), 49.92 (C-9'), 49.62 (C-1), 49.72 (C-3), 49.62 (C-12), 47.52 (C-14), 42.20 (C-4'), 39.65 (C-16'), 39.42 C-24'), 38.56 (C-8), 36.93 (C-1'), 36.45 (C-22'), 36.09 (C-8'), 35.69 (C-20'), 31.78 (C-7'), 28.14 (C-2'), 27.88 (C-25'), 27.74 (C-2), 24.19 (C-12'), 23.74 (C-15'), 22.75 (C-23'), 22.49 (C-26'), 20.95 (C-11'), 19.26 (C-19'), 18.64 (C-21'), 11.77 (C-18'); m/z (FAB) 672 (M+H)$^+$, 570, 539, 369 (Chol)$^+$, 84 (Found: (M+H)$^+$, 672.6205. C$_{41}$H$_{78}$N$_5$O2 requires (M+H)$^+$, 672.6156).

N$^1$-cholesteryloxy-carbonyl-4,9-diaza-1,12-dodecanediamine (CDAD) [B185] 13f'

$v_{max}$ (CH$_2$Cl$_2$) 3349, 2937, 2868, 1697, 1468, 1378 and 1253 cm$^{-1}$; $\delta_H$ (400 MHz) 5.70 (1H, br s, NHCO), 5.27 (1H, m, H-6'), 4.38 (1H, m, H-3'), 3.28–3.14 (6H, m, H-1, H-4, H-9, NH$_2$), 2.71 (2H, t, J 6.5 Hz, H-12), 2.63–2.52 (8H, m, H-3, H-5, H-8, H-10), 2.33–2.17 (2H, m, H-4'), 1.93–1.85 (5H, m, H-2', H-7', H-8'), 1.77–1.07 (29H, m, H-2, H-6, H-7, H-11, H-1', H-9', H-11', H-12', H-14' to H-17, H-20', H-22' to H-25'), 1.03 (3H, s, H-19'), 0.97 (3H, d, J 6.0 Hz, H-21'), 0.77 (6H, dd, J 5.0 and 1.5 Hz, H-26' and H-27'), 0.59 (3H, s, H-18'); $\delta_C$(100 MHz) 156.25 (NHC(O)O), 139.77 (C-5'), 122.26 (C-6'), 73.87 (C-3'), 56.57 (C-14'), 56.04 (C-17'), 49.90 (C-1), 49.60 (C-9'), 49.47 (C-3), 47.40 (C-10), 42.19 (C-4'), 39.63 (C-16'), 39.40 (C-24'), 38.55 (C-8), 36.92 (C-S), 36.44 (C-22'), 36.08 (C-8'), 35.69 (C-20'), 31.77 (C-7'), 28.13 (C-2'), 27.87 (C-25'), 27.53 (C-2), 24.18 (C-16), 23.74 (C-12'), 22.73 (C-23'), 22.48 (C-26'), 20.94 (C-11'), 19.25 (C-19'), 18.62 (C-21'), 11.76 (C-18'); m/z (FAB) 615 (M+H)$^+$, 539, 369 (Chol)$^+$, 57 (Found: (M+H)$^+$, 615.5626. C$_{38}$H$_{71}$N$_4$O$_2$ requires (M+H)$^+$, 615.5577).

N$^{15}$-cholesteryloxycarbonyl-3,7,12-triaza-1,15-pentadecanediamine (CTAP)[B232] 17a'

$v_{max}$ (CH$_2$Cl$_2$) 3568–3295, 2937, 1690, 1537, 1467, 1380, 1130 and 1019 cm$^{-1}$; $\delta_H$ (300 MHz) 5.76 (1H, br s, NHCO), 5.22 (1H, m, H-6'), 4.32 (1H, m, H-3'), 3.21 (2H, m, H-15), 2.65 (2H, t, J 5.5 Hz, H-13), 2.56–2.45 (12H, m, H-1, H-2, H-4, H-6, H-8, H-11), 2.18–2.05 (2H, m, H-4'), 1.97–1.67 (10H, m, H-3, H-7, H-12, H-2', H-7', H-8', NH$_2$), 1.59–0.91 (29H, m, H-5, H-9, H-10, H-14, H-1', H-9', H-11', H-12', H-14' to H-17', H-20', H-22' to H-25'), 0.86 (3H, s, H-19'), 0.77 (3H, d, J 6.5 Hz, H-21'), 0.72 (6H, dd, J 6.0 and 1.0 Hz, H-26' and H-27'), 0.53 (3H, s, H-18'); $\delta_C$(75 MHz) 156.24 (NHC(O)O), 139.77 (C-5), 122.21 (C-6'), 73.81 (C-3'), 56.57 (C-14'), 56.05 (C-17'), 49.91 (C-9'), 49.67 (C-15), 48.20 (C-13), 42.19 (C-4'), 39.64 (C-16'), 39.40 (C-24'), 38.56 (C-2), 36.92 (C-1'), 36.43 (C-22'), 36.08 (C-8'), 35.68 (C-20'), 31.77 (C-7'), 28.12 (C-2'), 27.86 (C-25'), 27.69 (C-14), 27.63 (C-5), 24.17 (C-12'), 23.74 (C-15'), 22.73 (C-23'), 22.48 (C-26'), 20.94 (C-11'), 19.25 (C-19'), 18.63 (C 21'), 11.76 (C-18'); m/z (FAB) 658 (M+H)$^+$, 539, 369 (Chol)$^+$, 95, 84 (Found: (M+H)$^+$, 658.6056. C$_{40}$H$_{76}$N$_5$O$_2$ requires (M+H)$^+$, 658.5999).

In Vitro and in Vivo Tests

For the in vitro and in vivo tests, a dried lipid film containing the given DC-Chol analogue and DOPE 2 (in either a 1:0, 1:1, 1:2 or 2:1 respective molar ratio), was hydrated for 10 min in sterile pyrogen-free water and then liposomes were produced by 2 min vortex mixing. The average diameter was between 200–400 nm.[32] Cationic liposomes containing DC-Chol 1 and DOPE 2 were formulated in the same way described previously.[24, 36]

Cationic liposome/plasmid DNA complexes were then prepared as follows.

Both cationic liposome suspensions and DNA (either pCF1-βGal plasmid expressing β-galactosidase or pCF1-CAT expressing chloramphenicol acetyl transferase)[32] solutions were separately pre-incubated for 5 min at 30° C., before being diluted to the appropriate final concentrations and then combined. Usually, cationic liposome suspensions were added to an approx. equal volume of plasmid DNA solutions. Complexes were allowed to equilibrate for a minimum of 15 min at ambient temperature and used within 2 h of preparation. In vitro and in vivo gene delivery assays were then performed as described previously using CFT1 cells and female BALB/c mice respectively.[32]

Discussion

In theory, genetic trait analysis will eventually be able to identify all the genetic loci which cause or contribute towards disease. With this information, corrective gene(s) may be identified which if introduced into the appropriate organs and cells of the body in vivo should correct the basic pathophysiological defect of the disease. This is the basic concept of gene therapy. Such a simple approach should be capable of curing the disease in contrast to most conventional pharmaceutical approaches which typically treat symptoms only.

However, introducing potentially corrective gene(s) is not straightforward. Whilst naked DNA may be administered under certain circumstances, for the most part a delivery vehicle or vector is required to effect efficient gene delivery. Several physical, chemical and virus-based vector systems are known but none are sufficiently efficacious for general use in human gene therapy. In spite of this, some vectors are showing some promise, in particular cationic liposome-based gene transfer systems.[21]

Cationic liposomes are heterogeneous, lipid vesicles typically formed from either a single cationic amphiphile (sometimes known as a cytofectin) or more commonly from a combination of a cationic amphiphile and a neutral lipid. They mediate gene delivery by interacting electrostatically with negatively charged DNA sequences forming complexes which may enter cells by endocytosis[22] or phagocytosis[23] and then release DNA for expression in the cell nucleus.[21] We have shown that cationic liposomes, formed from the cationic amphiphile 3β-[N-(N',N'-dimethyl-aminoethane)-carbamoyl]cholesterol (DC-Chol) 1 and the neutral phospholipid dioleoyl L-α-phosphatidylethanolamine (DOPE) 2, were able to transfect the lungs of mice in vivo.[24] Since then, some preparatory human clinical trials have been performed using similar DC-Chol/DOPE cationic liposomes.[25]

Both sets of experiments represent a proof of principle demonstrating that gene therapy with cationic liposomes is possible. However, both sets of experiments also showed that DC-Chol/DOPE cationic liposomes are unlikely to be efficient enough at gene delivery for general use in human gene therapy. Moreover, it is difficult to make improvements in the absence of any understanding of cationic liposome structure/activity relationships.

The present invention seeks to improve the earlier studies. In addition, the present invention seeks to understand some of the underlying chemical principles behind liposome-mediated gene delivery.

In this regard, a systematic series of DC-Chol analogues were made which could be incorporated into cationic liposomes and evaluated for gene delivery.

In conclusion, we have developed a flexible synthetic route to DC-Chol polyamine analogues which has allowed us to identify analogues with optimised methylene group spacing between amine functional groups for both in vitro and in vivo gene delivery. On the whole, so far we have found that unnatural spacing appears to work better. Without wishing to be bound by theory, perhaps, such polyamines have a slightly weakened interaction with DNA which facilitates the release of DNA into the cytoplasm, after transfer of the cationic liposome/DNA complex across the outer cell membrane.

At present, evidence so far suggests that our preferred DC-Chol analogue for in vivo studies and application is $N^{15}$-cholesteryloxycarbonyl-3,7,12-triaza-1,15-pentadecane-diamine (CTAP) 17a'. This compound is a novel pentamine of a type not previously shown to transfect cells. The efficacy of this compound appears to meet the necessary levels apparently required for a cytofectin to have realistic potential clinical use.[21,24,25,32]

SUMMATION

In summation, in the above examples liposomes were prepared from compounds comprising a cholesterol component and a head group component. The design of the compounds, which were used as cationic lipids, concentrated on the direct manipulation of the head group. With these compounds, the presence of the carbamoyl linkage is believed to be advantageous for low cytotoxicity and the presence of cholesterol is believed to be advantageous for the stabilisation of the liposomal bilayer. In these studies, we were able to alter the identity of the head group in order to increase the net positive charge of the liposome. Increasing the net positive charge is advantageous because it is believed to increase the DNA binding ability and the efficiency of gene transfer of the resultant liposome.

Other modifications of the present invention will be apparent to those skilled in the art.

References

1. W F Anderson, Science, 1992, 256, 808.
2. F D Ledley, Current Opinion in Biotechnology, 1994, 5, 626; K F Kozarsky, et al, ibid, 1993, 3, 499; Gordon, et al, ibid, 1994, 5, 611.
3. C P Hodgon, BioTech, 1995, 13, 222.
4. P L Feigner, et al, Proc Natl Acad Sci USA, 1987, 84, 7413; Felgner, et al, Nature, 1989, 337, 387; H-J Burger, et al, Proc Natl Acad Sci USA, 1992, 89, 2145.
5. Malone, et al, Proc Natl Acad Sci USA, 1989, 86, 6077.
6. M-Y Chiang, et al, J Biol Chem, 1991, 226, 18162.
7. R J Debs, et al, J Biol Chem, 1990, 265, 10189; C Walker, et al, Proc Natl Acad Sci USA, 1992, 89, 7915.
8. A D Bangham, Hospital Practice, 1992, 27, 51.
9. J-P, Behr, et al, Proc Natl Acad Sci USA, 1989, 86, 6982; R Leventis, et al, Biochim Biophys Acta, 1990, 1023, 124.
10. X Gao, et al, Gene Therapy, 1995, 2, 710.
11. R Stribling, et al, Proc Natl Acad Sci USA, 1992, 89, 11277.
12. E W F W Alton, et al, Nature Genetics, 1993, 5, 135.
13. X Gao, et al, Biochim Biophys Res Commun, 1991, 179, 280.
14. J E Morgan, et al, Arch Biochem Biophys, 1986, 246, 225.
15. A E Pegg, Biochem, 1986, 234, 249.
16. H Staudinger, et al, Helv Chim Acta, 1919, 2, 635; S Knapp, et al, J Org Chem, 1992, 57, 6239
17. K Omura, et al, Tetrahedron, 1978, 34, 1651.
18. J K Guy-Caffey, et al, J Biol Chem, 1995, 270, 31391.
21. a) X. Gao, L. Huang, Gene Ther. 1995, 2, 710–722, and references therein; b) A. D. Miller, R. G. Cooper, C. J. Etheridge, L. Stewart in Microspheres, Microcapsules and Liposomes (Ed. R. Arshady), John Wiley & Sons, 1997, in press, and references therein; c) P. L. Felgner, Hum. Gene Ther. 1996, 7, 1791–1793.
22. a) H. Farhood, N. Serbina, L. Huang, Biochim. Biophys. Acta 1995, 1235, 289–295; b) J. Zabner, A. J. Fasbender, T. Moninger, K. A. Poellinger, M. J. Welsh, J. Biol. Chem. 1995, 270, 18997–19007.
[23]. H. Mitsui, L. G. Johnson, S. H. Randell, R. C. Boucher, J. Biol. Chem. 1997, 272, 1117–1126.
24. E. W. F. W. Alton, P. G. Middleton, N. J. Caplen, S. N. Smith, D. M. Steel, F. M. Munkonge, P. K. Jeffery, D. M. Geddes. S. L. Hart, R. Williamson, K. I. Fasold, A. D. Miller, P. Dickinson, B. J. Stevenson, G. McLachlan, J. R. Dorin, D. J. Porteous, Nature Genetics 1993, 5, 135–142.
25. a) N. J. Caplen, E. W. F. W. Alton, P. G. Middleton, J. R. Dorin, B. J. Stevenson, X. Gao, S. R. Durham, P. K. Jeffery, M. E. Hodson, C. Coutelle, L. Huang, D. J. Porteous, R. Williamson, D. M. Geddes, Nature Medicine 1995, 1, 39–46; b) G. J. Nabel, E. G. Nabel, Z.-y. Yang, B. A. Fox, G. E. Plautz, X. Gao, L. Huang, S. Shu, D. Gordon, A. E. Chang, Proc. Natl. Acad. Sci. USA 1993, 90, 11307–11311.
26. Liposomes: a practical approach (Ed.: R. R. C. New), IRL Press, Oxford, 1990.
27. J. H. Felgner, R. Kumar, C. N. Sridhar, C. J. Wheeler, Y. J. Tsai, R. Border, P. Ramsey, M. Martin, P. L. Felgner, J. Biol. Chem. 1994, 269, 2550–2561.
28. K. Omura, D. Swern, Tetrahedron 1978, 34, 1651–1660.
29. S. Knapp, J. J. Hale, M. Bastos, A. Molina, K. Y. Chen, J. Org. Chem. 1992, 57, 6239–6256

30. (a) H. Staudinger, J. Meyer, Helv. Chim. Acta 1919, 2, 635–646; (b) E. Fabiano, B. T. Golding, M. M. Sadeghi, Synthesis 1987, 190–192; (c) B. T. Golding, M. C. O'Sullivan, L. L. Smith, Tetrahedron Lett. 1988, 29, 6651–6654; (d) Y. G. Gololobov, L. F. Kasukhin, Tetrahedron 1992, 48, 1353–1406; (e) A. W. Johnson, W. C. Kaska, K. A. O. Starzewski, D. A. Nixon, Ylides and Imines of Phosphorus (Ed.: A. W. Johnson), J. Wiley and Sons, New York, 1993. chap. 13, pp. 403–483.

31. (a) J. E. Baldwin, R. M. Adlington, A. S. Elend, M. L. Smith, Tetrahedron 1995, 51, 11581–11594; (b) R. M. Moriarty, S. M. Tuladhar, L. Guo, S. Wehrli, Tetrahedron Lett. 1994, 35, 8103–8106.

32. E. R. Lee, J. Marshall, C. S. Siegel., C. Jiang, N. S. Yew, M. R. Nichols, J. B. Nietupski, R. J. Ziegler, M. B. Lane, K. X. Wang, N. C. Wan, R. K. Scheule, D. J. Harris, A. E. Smith, S. H. Cheng, Hum. Gene Ther. 1996, 7, 1701–1717.

33. C. J. Wheeler, P. L. Felgner, Y. J. Tsai, J. Marshall, L. Sukhu, S. G. Doh, J. Hartikka, J. Nietupski, M. Manthorpe, M. Nichols, M. Plewe, X. Liang, J. Norman, A. Smith, S. H. Cheng, Proc. Natl. Acad. Sci. USA 1996, 93, 11454–11459.

34. J. K. Guy-Caffey, V. Bodepudi, J. S. Bishop, K. Jayaraman, N. Chaudhary, J. Biol. Chem. 1995, 270, 31391–31396.

35. a) J.-P. Vigneron, N. Oudrhiri, M. Fauquet, L. Vergely, J.-C. Bradley, M. Basseville, P. Lehn, J.-M. Lehn, Proc. Natl. Acad. Sci. USA 1996, 93, 9682–9686; b) J. G. Lewis, K.-Y. Lin, A. Kothavale, W. M. Flanagan, M. D. Matteucci, B. De Prince, R. A. Mook Jr., R. W. Hendren, R. W. Wagner, ibid 1996, 93, 3176–3181; c) D. Moradpour, J. I. Schauer, V. R. Zurawski Jr., J. R. Wands, R. H. Boutin, Biochem. Biophys. Res. Commun. 1996, 221, 82–88.

36. X. Gao. L. Huang, Biochem. Biophys. Res. Commun. 1991, 179, 280–285.

What is claimed is:

1. A cationic lipid compound, the compound comprising a cholesterol group or derivative thereof having linked thereto a head group;
   wherein the head group is more positive than the head group of DC-Chol;
   further wherein the head group is a polyamine group which is a straight chain polyamine group further wherein two or more of the amine groups of the polyamine group are separated by an ethylene group.

2. A compound according to claim 1 wherein the cholesterol group or derivative thereof is cholesterol.

3. A compound according to claim 1 wherein the cholesterol group is linked to the head group via a carbamoyl linkage.

4. A compound according to claim 1 in admixture with or associated with a nucleotide sequence.

5. A process for preparing a cationic lipid compound according to claim 1 wherein the process comprises reacting cholesterol group with a head group of claim 1 to prepare the said cationic lipid compound.

6. The process of claim 5 wherein the cholesterol group or derivative thereof is cholesterol.

7. The process of claim 5 wherein the cholesterol group is linked to the head group via a carbamoyl linkage.

8. The process of claim 5 wherein the reacting step comprises utilizing aza-Wittig methodology.

9. A method of manufacturing a medicament, the method comprising the step of formulating a transfection effective amount of a compound of claim 1 and a pharmaceutically acceptable diluent, carrier or excipient into a medicament to manufacture a medicament comprising a transfection effective amount of the compound of claim 1.

10. A cationic liposome formed from a cationic lipid compound, the compound comprising a cholesterol group having linked thereto a head group; wherein the head group is more positive than the head group of DC-Chol; further wherein the head group is a polyamine group which is a straight chain polyamine group further wherein two or more of the amine groups of the polyamine group are separated by an ethylene group.

11. A cationic liposome according to claim 10 wherein the cholesterol group of the compound capable of acting as a cationic lipid is cholesterol.

12. A cationic liposome according to claim 10 wherein the cholesterol group of the cationic lipid compound is linked to the head group via a carbamoyl linkage.

13. A cationic liposome according to claim 10 in admixture with or associated with a nucleotide sequence.

14. A method of manufacturing a medicament, the method comprising the step of formulating a transfection effective amount of a cationic liposome of claim 10 and a pharmaceutically acceptable diluent, carrier or excipient into a medicament to manufacture a medicament comprising a transfection effective amount of the cationic liposome of claim 10.

15. The method of claim 9, further wherein a nucleotide sequence is combined in the medicament.

16. The method of claim 14, further wherein a nucleotide sequence is combined in the medicament.

17. A pharmaceutical composition comprising a compound according to claim 1, a pharmaceutical and, optionally, a pharmaceutically acceptable diluent, carrier or excipient.

18. The pharmaceutical composition of claim 17 wherein the cholesterol group or derivative thereof in the compound according to claim 1 is cholesterol.

19. A pharmaceutical composition comprising a cationic liposome according to claim 10, a pharmaceutical and, optionally, a pharmaceutically acceptable diluent, carrier or excipient.

20. A compound of claim 1 of the formula

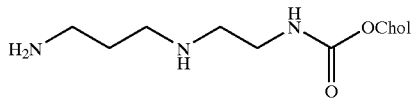

21. A compound of claim 1 of the formula

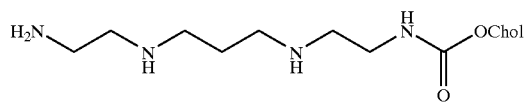

22. A compound of claim 1 of the formula

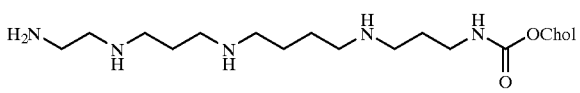

* * * * *